US012594232B2

(12) United States Patent
Karagianni et al.

(10) Patent No.: US 12,594,232 B2
(45) **Date of Patent: *Apr. 7, 2026**

(54) PERSONAL CARE COMPOSITIONS AND METHODS FOR USING SUCH COMPOSITIONS

(71) Applicant: SPECIALTY OPERATIONS FRANCE, Lyons (FR)

(72) Inventors: Katerina Karagianni, Paris (FR); Denis Bendejacq, Philadelphia, PA (US)

(73) Assignee: SPECIALTY OPERATIONS FRANCE, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/091,212

(22) PCT Filed: Apr. 5, 2017

(86) PCT No.: PCT/EP2017/058148

§ 371 (c)(1),
(2) Date: Oct. 4, 2018

(87) PCT Pub. No.: WO2017/174675

PCT Pub. Date: Oct. 12, 2017

(65) Prior Publication Data

US 2019/0110979 A1 Apr. 18, 2019

(30) Foreign Application Priority Data

Apr. 8, 2016 (EP) .................................... 16164499

(51) Int. Cl.

| | |
|---|---|
| ***A61K 8/92*** | (2006.01) |
| ***A61K 8/365*** | (2006.01) |
| ***A61K 8/37*** | (2006.01) |
| ***A61K 8/46*** | (2006.01) |
| ***A61K 8/86*** | (2006.01) |
| ***A61Q 5/02*** | (2006.01) |
| ***A61Q 5/12*** | (2006.01) |
| ***A61Q 19/10*** | (2006.01) |
| *A61K 8/89* | (2006.01) |

(52) U.S. Cl.

CPC .............. *A61K 8/922* (2013.01); *A61K 8/365* (2013.01); *A61K 8/37* (2013.01); *A61K 8/466* (2013.01); *A61K 8/86* (2013.01); *A61Q 5/02* (2013.01); *A61Q 5/12* (2013.01); *A61Q 19/10* (2013.01); *A61K 8/89* (2013.01); *A61K 2800/262* (2013.01); *A61K 2800/49* (2013.01); *A61K 2800/596* (2013.01)

(58) Field of Classification Search

None

See application file for complete search history.

(56) References Cited

U.S. PATENT DOCUMENTS

| | | | | |
|---|---|---|---|---|
| 5,696,069 | A * | 12/1997 | Ito | A61K 8/39 510/123 |
| 6,759,056 | B2 | 7/2004 | Jordan | |
| 6,946,144 | B1 | 9/2005 | Jordan | |
| 7,201,919 | B2 | 4/2007 | Jordan | |
| 7,220,427 | B2 | 5/2007 | Jordan | |
| 7,300,666 | B2 | 11/2007 | Jordan | |
| 7,316,820 | B2 | 1/2008 | Jordan | |
| 2005/0164896 | A1 | 7/2005 | Dabkowski et al. | |
| 2008/0095733 | A1* | 4/2008 | Griffin | A61Q 19/10 424/70.19 |
| 2012/0021025 | A1* | 1/2012 | Bendejacq | A61K 8/0295 424/401 |

FOREIGN PATENT DOCUMENTS

| | | | |
|---|---|---|---|
| EP | 1765310 | B1 | 10/2015 |
| EP | 1684681 | B1 | 10/2018 |
| KR | 20090056321 | A | 6/2009 |
| WO | 9932079 | | 7/1999 |
| WO | 2005039464 | A1 | 6/2005 |
| WO | 2006041538 | A2 | 4/2006 |
| WO | 2006041538 | A3 | 4/2006 |
| WO | 2017174678 | A1 | 10/2017 |

OTHER PUBLICATIONS

Database GNPD Mintel; Sep. 1, 2014 (Sep. 1, 2014), "Shampoo", XP002760442, Database accession No. 2677439.

Cynthia Dulude: "Produits capillaires CHI à Huile d'Argan", Dec. 29, 2014 (Dec. 29, 2014), XP002769945, Retrieved from the Internet <URL:http://www.maquillagecynthia.com/produits/articles-produits/produits-capillaires-chi-huile-dargan/>.

Annex issued Jul. 25, 2023 in European Patent Application No. 17714820.2.

Summons to Attend Oral Proceedings issued Jul. 25, 2023 in European Patent Application No. 17714820.2.

* cited by examiner

*Primary Examiner* — Celeste A Roney

(74) *Attorney, Agent, or Firm* — Vorys, Sater, Seymour and Pease LLP; Maryellen Feehery Hank; Anthony P. Venturino

(57) ABSTRACT

The present invention relates to a cosmetic cleansing composition comprising at least: a) one or more vegetable oil(s), in an amount of at least 0.3 pbw relative to the total weight of the composition, b) from about 2 pbw to about 40 pbw, relative to the total weight of the composition, of a surfactant system comprising at least one sultaine surfactant and one taurate surfactant, and c) at least 0.1 pbw, relative to the total weight of the composition, of a non-ionic solubilizer which is a mono- or poly-alkyl or alkenyl ester of an alkoxylated fatty acid.

25 Claims, No Drawings

PERSONAL CARE COMPOSITIONS AND METHODS FOR USING SUCH COMPOSITIONS

This application is a U.S. national phase entry under 35 U.S.C. § 371 of International Application No. PCT/EP2017/058148, filed on Apr. 5, 2017, which claims priority to European application No. 16164499.2 filed on Apr. 8, 2016. The entire contents of these applications are explicitly incorporated herein by this reference.

The present invention relates to personal care compositions and methods for using such compositions.

In particular the present invention relates to cosmetic compositions exhibiting both conditioning and cleansing properties for the simultaneous care and washing of keratinous materials.

Cosmetic cleansing compositions based essentially on conventional surface-active agents of, in particular, anionic, non-ionic and/or amphoteric type, are used for washing keratinous materials, such as the hair and/or the skin. Typical examples of cosmetic cleansing compositions include body care compositions such as shower gels, facial cleansers, body-washes, liquid hand soaps, and hair care compositions such as shampoos and cleansing conditioners.

These compositions are applied to wet hair or skin and the foam generated by massaging or rubbing with the hands makes it possible, after rinsing with water, to remove dirt initially present on the hair or the skin.

Although having good washing power, these base compositions possess cosmetic properties that remain fairly weak, in particular as the relatively aggressive nature of such a cleansing treatment can result, in the long term, in more or less marked damage to the keratinous materials, damage related in particular to the gradual removal of the lipids or proteins present in or at the surface of these keratinous materials.

This is the reason why most of the cosmetic cleansing compositions further comprise additional cosmetic agents known as conditioners, which are intended mainly to repair or limit the harmful or undesirable effects brought about by the various treatments or attacks to which keratinous materials are more or less repeatedly subjected. These conditioners can also improve the cosmetic behavior of the keratinous materials.

The most commonly used conditioners, especially in hair care formulations, are cationic polymers, silicones and/or silicone derivatives.

In recent times there is an increasing demand for personal care compositions including safe, environment friendly and/or natural conditioners, and especially for personal care compositions containing vegetable oils as main conditioners.

Using vegetable oils in the formulation of cosmetic compositions has been known from early times. Vegetable oils are endowed with emollient and moisturizing properties and impart great softness to the skin. They are also already known to confer conditioning on hair, such as an increased ease of detangling or softness.

Also, in hair care formulations, vegetable oils generally confer a better softness of the hair and/or a better smoothness (hair being uniform from the root to the tip) compared to formulations including conventional cationic polymers, silicones and/or silicone derivatives as main conditioners.

There is a need however to solubilize vegetable oils in a relative high amount, typically of at least 0.3 pbw relative to the total weight of the composition, in order to really benefit from their conditioning properties, especially when vegetable oils are used as main conditioners.

However, incorporating relative high amounts of vegetable oils in cleansing personal care compositions generally negatively impacts other attributes, such as foaming properties or viscosity of the overall composition, and/or may also lead to adverse effects, such as an unacceptable greasy feel to the composition or on the target area.

Furthermore, clear or transparent cosmetic compositions are particularly desirable because the consumer likens transparency to purity. Transparent formulations also have aesthetic appeal generally speaking.

However, incorporating relative high amounts of vegetable oils in cleansing personal care compositions may be detrimental to transparency.

This is the reason one of the major challenges when incorporating relative high amounts of vegetable oils into a cosmetic composition is to benefit from the conditioning properties of vegetable oils while maintaining satisfactory foaming properties and without negatively impacting viscosity and/or transparency of the overall composition.

It is thus an object of the present invention to address the ever increasing demand in the market for personal care cleansing and conditioning compositions which are preferably transparent and that contain relative high amounts of vegetable oils, while maintaining satisfactory viscosity and foaming properties.

Another object of the present invention is to provide personal care cleansing and conditioning compositions which are preferably transparent, which are sufficiently foaming and which exhibit good conditioning properties, such as ease of detangling, softness and shine properties, and a satisfactory viscosity.

The Application has now discovered unexpectedly that a personal care composition containing a particular combination of surfactants, one of which is a taurate surfactant and the another one of which is a sultaine surfactant, together with a specific solubilizer, makes it possible to achieve the objective as outlined above.

All amounts are in parts by weight (pbw) relative to the total weight of the composition.

The subject of the invention is thus a cosmetic cleansing composition comprising at least:

a) one or more vegetable oil(s), in an amount of at least 0.3 pbw relative to the total weight of the composition,
b) from about 2 pbw to about 40 pbw, relative to the total weight of the composition, of a surfactant system comprising at least one sultaine surfactant and one taurate surfactant, and
c) at least 0.1 pbw, relative to the total weight of the composition, of a non-ionic solubilizer which is a mono- or poly-alkyl or alkenyl ester of an alkoxylated fatty acid.

The present invention is also directed toward the use of such a composition for simultaneously caring for and washing keratinous materials, such as the hair and the skin.

Surprisingly it has been found that the specific surfactant mixture and solubilizer used in the composition according to the invention makes it possible to formulate relative high amounts of vegetable oils and to achieve at the same time an acceptable compromise between the following attributes: viscosity of the composition, foaming properties and conditioning on target area, while maintaining transparency.

The compositions of the invention can confer on keratinous materials, in particular the hair, a noteworthy treating effect which is revealed in particular by an ease of detangling, as well as a contribution on softness and shine without major feeling of greasiness.

Also, when applied to the skin, such as in the form of a bubble bath or a shower gel, the composition of the invention can give for example an improvement in the softness of the skin.

The foam properties (such as appearance, consistency, abundance of the foam and/or elimination of the foam) and viscosity of the compositions of the invention are also satisfactory. Especially the composition of the invention allow an acceptable spreading onto keratin materials.

By the expression "composition having a satisfactory viscosity" it is meant here a composition that has an apparent viscosity comprised between 1,500 and 50,000 cps, for instance comprised between 2,000 and 30,000 cps, for instance comprised between 2,000 and 25,000 cps, for instance comprised between 2,500 and 20,000 cps. The apparent viscosity of each composition was measured after 24-hours in a temperature-controlled room (21±3° C.), using a Brookfield Viscosimeter Model DV-I at 10 RPM, with a RV spindle 4. The viscosity value was always taken after a stabilization time of 1 min.

According to one embodiment, the composition of the invention has an apparent viscosity greater than 1,500 cps, for instance greater than 2,000 cps.

By the expression "transparent composition" it is meant here a composition exhibiting a clear, transparent visual appearance, for example exhibiting a light transmittance value at 600 nm of greater than or equal to 85%, preferably of greater than or equal to 88% and more preferably greater than or equal to 90%.

Transmittance (% T) may be measured at 600 nm in 2.5 ml polystyrene cell, 10×10 mm, using a UV/VIS spectrometer Lambda Bio 40.

According to anyone of the invention embodiments, a composition of the invention is a transparent composition.

However, within the scope of the invention are compositions which are not themselves transparent because they further comprise one or more additives that adversely affect transparency, such as for instance pearlising and/or opacifying agents.

By the expression "foaming properties" it is meant especially here flash foam and foam volume, which are among the main factors affecting the consumer perception about the foam quality. Well-known tests, notably as described in the experimental part, may be used to measure these factors.

By the expression "conditioning on target area" it is meant imparting positive properties to the target area. The target area may be especially a keratinous material. As used herein, "keratinous materials" include, but are not limited to, skin, hair, scalp, lips, eyelashes and nail. Preferably the target area is skin, hair and/or scalp.

For example in the case where the target area is hair "improved conditioning" may cover improved ease of detangling and/or ease of combing, softness and/or shine.

Ease of detangling may be determined by the measurement of the time required for detangling the hair. The shorter the detangling time, the easier to detangle the hair is.

Ease of combing may be determined by the measurement of the work required for combing the hair. The lower the combing work, the easier to comb the hair is.

Softness, or hair feel, and shine may be assessed by an expert panel using sensorial tests on hair care on length and tips.

Alternatively in the case where the target area is skin, "improved conditioning" may cover improved moisturizing properties.

Moisturizing properties may be determined by sensorial tests which are well known by the skilled person.

By the expression "oil", it is meant a fatty compound or substance which is in the form of a liquid or a paste (non-solid) at room temperature (25° C.) under atmospheric pressure (760 mmHg).

The composition of the invention is a personal care composition, preferably a personal care cleansing composition, that is to say a composition aimed to the washing/cleaning and in particular for a body-care application, such as but not limited to a shower gel, a facial cleanser, a body-wash, a liquid hand soap, a shampoo or a cleansing conditioner.

Elsewhere in the specification and claims, individual numerical values, or limits, can be combined to form additional non-disclosed and/or non-stated ranges For the avoidance of any doubt the amounts of surfactant refer to the actual amount of active surfactant compound present in the composition. In other words, it does not include the residue which may be present as an impurity in a commercially available surfactant mixture.

Should the disclosure of any patents, patent applications, and publications which are incorporated herein by reference conflict with the description of the present application to the extent that it may render a term unclear, the present description shall take precedence.

Vegetable Oil(s)

A composition of the present invention comprises one or more vegetable oil(s), which may be volatile or non-volatile.

Vegetable oils (natural, native oils) are understood to be preferably triglycerides and mixtures of triglycerides.

The minimum content of vegetable oil(s), preferably non-volatile vegetable oil(s), in a composition according to the present invention is 0.3 pbw.

According to anyone of the invention embodiments, a composition of the invention comprises at least one non-volatile vegetable oil.

A non-volatile vegetable oil according to the invention is an oil which exhibits a boiling temperature generally greater than 300° C. at 760 mm of Hg and which does not exhibit or which exhibits a very low vapor pressure. In particular, essential oils, which are volatile oils, are not within the definition of non-volatile vegetable oils according to the invention.

Preferred vegetable oils are coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter, shea butter, kukui oil and/or mixtures of these oils.

Typical examples of oils of vegetable origin that can be used include the following (INCI names): Adansonia Digitata Seed Oil, Aleurites Molluccana Seed Oil, Alpinia Speciosa Leaf Oil, Argemone Mexicana Oil, Brassica Oleracea Italica (Broccoli) Seed Oil, Calodendrum Capense Nut Oil, Calophyllum Inophyllum Seed Oil, Camellia Chekiangoleosa Seed Oil, Carica Papaya Seed Oil, Cedrus Deodara Seed Oil, Cocos Nucifera (Coconut) Oil, Crambe Abyssinica Seed Oil, Egg Oil, Fragaria Ananassa (Strawberry) Seed Oil, Hydrogenated Camellia Oleifera Seed Oil, Hydrogenated Evening Primrose Oil, Hydrogenated Hazelnut Oil, Hydrogenated Lanolin, Hydrogenated Macadamia Seed Oil, Hydrogenated Rice Bran Oil, Hydrogenated Sesame Seed Oil, Hydroxylated Jojoba Oil, Isobutylated Lanolin Oil Lanolin Oil, Lesquerella Fendleri Seed Oil, Marmot Oil, Mink Oil, Ocimum Tenuiflorum Oil, Orbignya Cohune Seed Oil, Ostrich Oil, Phormium Tenax Seed Oil, PPG-40-PEG-60 Lanolin Oil, PPG-12-PEG-65 Lanolin Oil, Pongamia Glabra Seed Oil, Pinus Parviflora Seed Oil, Sclerocarya Birrea Seed Oil, Schleichera Trijuga Seed Oil, Simmondsia Chinensis (Jojoba) Seed Oil, Sorbus Aucuparia Seed Oil, Zea Mays (Corn) Oil, Bertholletia Excelsa Seed Oil PEG-8 Esters, Coconut Oil Methylpropanediol Esters, Jojoba Oil PEG-8 Esters, Hydrogenated Castor Oil Behenyl Esters, Hydrogenated Castor Oil Cetyl Esters, Hydrogenated Castor Oil Dimer Dilinoleate, Hydrogenated Castor Oil Stearyl Esters, Hydrogenated Olive Oil Caprylyl Esters, Hydrogenated Olive Oil Cetyl Esters, Hydrogenated Olive Oil Decyl Esters, Hydrogenated Olive Oil Hexyl Esters, Hydrogenated Olive Oil Lauryl Esters, Hydrogenated Olive Oil Myristyl Esters, Hydrogenated Olive Oil Stearyl Esters, Orbignya Oleifera Seed Oil PEG-8 Esters, Passiflora Edulis/Passiflora Incarnata Seed Oils PEG-8 Esters, Brassica Campestris (Rapeseed) Oil Unsaponifiables, Brassica Oleracea Botrytis (Cauliflower) Oil Unsaponifiables, Butyrospermum Parkii (Shea Butter) Unsaponifiables, Canola Oil Unsaponifiables, Citrus Aurantifolia (Lime) Seed Oil Unsaponifiables, Citrus Aurantium Dulcis (Sweet Orange) Seed Oil Unsaponifiables, Citrus Grandis (Grapefruit) Seed Oil Unsaponifiables, Hydrogenated Apricot Oil Unsaponifiables, Hydrogenated Grapefruit Seed Oil Unsaponifiables, Hydrogenated Lime Seed Oil Unsaponifiables, Hydrogenated Olive Oil Unsaponifiables, Hydrogenated Orange Seed Oil Unsaponifiables, Hydrogenated Sweet Almond Oil Unsaponifiables, Hydrogenated Wheat Germ Oil Unsaponifiables, Helianthus Annuus (Sunflower) Seed Oil Unsaponifiables, Lupinus Albus Oil Unsaponifiables, Medicago Sativa (Alfalfa) Oil Unsaponifiables, Olea Europaea (Olive) Oil Unsaponifiables, Olea Europaea (Olive) Fruit Unsaponifiables, Persea Gratissima (Avocado) Oil Unsaponifiables, Prunus Armeniaca (Apricot) Kernel Oil Unsaponifiables, Sesamum Indicum (Sesame) Oil Unsaponifiables, Triticum Vulgare (Wheat) Germ Oil Unsaponifiables, Zea Mays (Corn) Oil Unsaponifiables.

The vegetable oils according to the present invention are preferably chosen from sunflower oil, avocado oil, jojoba oil, maize oil, sweet almond oil, soybean oil, cucumber oil, grape seed oil, sesame oil, hazelnut oil, palm oil, castor oil, walnut oil, coconut oil, apricot oil, olive oil, kukui oil, cashew nut oil and purcellin oil.

According to a preferred embodiment, the vegetable oils are preponderantly present in the oily phase of the composition of the present invention.

Thus, according to this embodiment, a composition of the invention comprises at least 50 pbw of vegetable oil(s), in particular at least 60 pbw, for example from 60 to 90 pbw, or even 100 pbw, of vegetable oil(s), relative to the total weight of the oily phase.

According to anyone of the invention embodiments, the composition of the invention comprises from 0.5 to 5 pbw of vegetable oil, relative to the total weight of the composition, for instance at least 0.6 pbw, for instance at least 0.7 pbw.

According to anyone of the invention embodiments, the vegetable oil is the main conditioner in a composition of the invention, that is to say that the weight percent in vegetable oil in a composition of the invention is greater than the weight percent in any other conditioner, for instance is greater than the weight percent in any silicone or mineral oil, or in any cationic or ampholytic conditioning agent.

Solubilizer

A composition of the present invention comprises at least one non-ionic solubilizer which is a mono- or poly-alkyl or alkenyl ester of an alkoxylated fatty acid.

Suitable fatty acids include saturated or unsaturated, hydroxylated or non-hydroxylated, (C8-C22), more typically (C12-C18), fatty acids and combinations thereof.

Typical examples of saturated or unsaturated hydroxylated (C8-C22) fatty acids include ricinoleic acid, lesquerolic acid, hydroxyerucic acid (16-hydroxydocos-cis-13-enoic acid) or hydroxypalmitoleic acid (12-hydroxyhexadec-cis-9-enoic acid), and combinations thereof.

Typical examples of saturated or unsaturated non-hydroxylated (C8-C22) fatty acids include myristic acid, palmitic acid, stearic acid, oleic acid, lauric acid, arachidic acid, behenic acid, linoleic acid, linolenic acid, margaric acid, and combinations thereof.

Preferably the fatty acid used as starting material is a saturated or unsaturated hydroxylated (C8-C22), typically (C12-C18), fatty acid. According to this embodiment, the non-ionic solubilizer of the invention is a mono- or poly-alkyl or alkenyl ester of an alkoxylated fatty acid, with said fatty acid being a saturated or unsaturated hydroxylated (C8-C22), typically (C12-C18), fatty acid.

Preferably the fatty acid used as starting material is an unsaturated hydroxylated (C8-C22), typically (C12-C18), fatty acid.

Typical examples of unsaturated hydroxylated (C8-C22) fatty acids include ricinoleic acid, lesquerolic acid or hydroxyerucic acid (16-hydroxydocos-cis-13-enoic acid).

In one of the invention embodiments, the solubilizer is a mono- or poly-alkyl or alkenyl ester of an alkoxylated fatty acid, with said fatty acid being a saturated or unsaturated hydroxylated (C8-C22) fatty acid, preferably a unsaturated hydroxylated (C8-C22), more typically (C12-C18), fatty acid.

Said fatty acid may be especially ricinoleic acid derived from natural sources, such as non hydrogenated castor oil. For instance, ricinoleic acid may be obtained from the saponification of castor oil.

When hydroxylated fatty acids, such as for instance ricinoleic acid, are used as starting materials, several hydroxyl groups may be alkoxylated, namely the hydroxyl group(s) on the fatty acid chain and the hydroxyl group from the carboxyl group.

Alkoxylation of hydroxylated fatty acids, such as for instance ricinoleic acid, gives thus rise to specific alkoxylated fatty acids, compared for instance to alkoxylated fatty acids obtained from non hydroxylated fatty acids.

The solubilizer of the invention is a mono- or poly-alkyl or alkenyl ester of an alkoxylated fatty acid as described previously, that is to say a mono- or poly-alkyl or alkenyl ester of a fatty acid as described previously that has been alkoxylated beforehand with from 2 or more moles of (C2-C4)alkylene oxide units per molecule.

Said fatty acid may have been alkoxylated beforehand with from, for instance 2 or more moles of ethylene oxide units, propylene oxide units, or ethylene oxide-propylene oxide units per molecule.

The number of (C2-C4) alkylene oxide units may for instance range from 2 to 500 moles per molecule, for instance from 5 to 250, for instance from 5 to 100, for instance from 5 to 50, for instance from 10 to 30.

In one of the invention embodiments, the solubilizer is a mono- or poly-alkyl or alkenyl ester of an (C2-C4), more typically C2, alkoxylated fatty acid as described previously, preferably a hydroxylated fatty acid, with the number of (C2-C4), more typically C2, alkylene oxide units ranges from 5 to 100, for instance from 5 to 50, for instance from 10 to 30.

The solubilizer of the invention is a mono- or poly-alkyl or alkenyl ester of an alkoxylated fatty acid as described previously, preferably a hydroxylated fatty acid, that is to say a mono- or poly-ester of such alkoxylated fatty acid with the ester moieties (i.e. the moieties derived from the acid that is to react with the hydroxyl group) being an alkyl or an alkenyl group.

The ester moieties may derive from fatty acids, wherein the fatty acid moiety has from about 8 to about 40 carbon atoms, for instance from about 12 to about 22 carbon atoms, for instance from about 14 to about 20 carbon atoms.

Non limiting examples of fatty acids suitable for making the ester moieties include acids such as myristic, palmitic, stearic, oleic, ricinoleic, lauric, arachidic, behenic, linoleic, linolenic, margaric, and combinations thereof. These fatty acids may be especially oleic acids, linoleic acid and palmitic acids derived from natural sources, such as palm oil.

In one of the invention embodiments, the solubilizer is a mono- or poly-alkenyl ester of an (C2-C4), more typically C2, alkoxylated fatty acid as described previously, preferably a hydroxylated fatty acid, such as ricinoleic acid, with the ester moiety being derived from fatty acids, such as oleic acid, derived from palm oil.

In one of the invention embodiments, the solubilizer is a mono- or poly-alkenyl ester of an (C2-C4), more typically C2, alkoxylated fatty acid as described previously, preferably a hydroxylated fatty acid, such as ricinoleic acid, with the number of alkylene oxide units per molecule ranging preferably from 10 to 30, and with the ester moiety being derived from fatty acids, such as oleic acid, preferably derived from palm oil.

The solubilizer of the invention is different from ethoxylated vegetable oils and from ethoxylated glyceryl esters.

The HLB of non ionic solubilizers or surfactants can be measured using the calculation method defined in the publication by W C Griffin, J. Soc. Cosm. Chem. 1954 (Vol. 5), 249-256 pages, ie $HLB=20\times Mh/M$, wherein Mh is the molecular weight of the hydrophilic portion of the molecule and M is the total molecular weight of the molecule giving a result on a scale of 0 to 20.

For non ionic solubilizers of the invention, the following formula may be used: $HLB=20\times(1-(A/B))$ where A=saponification number of the ester and B=acid number of the acid.

An HLB value of 0 calculated according to the Griffin method corresponds to a completely lipophilic/hydrophobic molecule, and a value of 20 corresponds to a completely hydrophilic/lipophobic molecule.

For anionic surfactants, the method of calculation defined in the publication Davies JT "A Quantitative Kinetic Theory of Emulsion types. I. Physical Chemistry of the Emulsifying Agent. "Gas/Liquid and Liquid/Liquid Interfaces. Proceedings of the 2nd International Congress Surface Activity (1957) 426-438 may be used.

According to anyone of the invention embodiments, the HLB (hydrophilic/lipophilic balance) at room temperature of the solubilizer of the invention is lower than 18, for instance lower than 16, for instance lower than 14, for instance lower than 12, for instance lower than 10, for instance lower than 8.

According to anyone of the invention embodiments, the HLB (hydrophilic/lipophilic balance) at room temperature of the solubilizer on the invention is greater than 2, for instance greater than 4, for instance greater than 6, for instance greater than 7.

According to anyone of the invention embodiments, the HLB (hydrophilic/lipophilic balance) at room temperature of the solubilizer of the invention is comprised between 5 and 10, for instance between 6 and 9, for instance between 7 and 8.

Solubilizers in accordance with the invention may be obtained by esterification of alkoxylated fatty acids, which are commercially available compounds. Such reactions can be implemented by conventional methods which are well known by the skilled person.

Examples of suitable solubilizers include PEG-18 CASTOR OIL DIOLEATE, which is an oleic acid diester of ethoxylated castor oil in which the average ethoxylation value is 18, and which is sold for instance under the name Marlowet CG.

Mention may be also made of PEG 16 CO Oleate available under the name Alkamuls PEG 16 CO sold by Solvay.

It has been found unexpectedly that the solubilizers of the invention are very efficient in formulating vegetable oils, while maintaining transparency of the composition.

Advantageously the solubilizers of the invention are also not detrimental to the conditioning properties of the composition. For instance, it has been found during the sensorial assessment that comparative solubilizers such as PEG-40 hydrogenated castor oil negatively impacts foam properties (foam is less rich) and softness (the hair is less soft in the dry state), compared to PEG-18 castor oil dioleate or PEG-16 CO Oleate.

The solubilizers of the invention are able to formulate high amounts of vegetable oils, even when they are present in the composition at relatively low weight ratios.

Advantageously, the solubilizer of the invention has also been developed to be efficient by itself with different types of natural oils, to avoid cocktails of solubilizers formulators usually have to resort to.

According to anyone of the invention embodiments, said solubilizer is present in a concentration ranging from 0.01 to 10 pbw relative to the total weight of the composition, for example from 0.1 to 5 pbw, for example from 0.2 to 3 pbw, for example from 0.3 to 2 pbw.

According to anyone of the invention embodiments, the weight ratio between the vegetable oil and the solubilizer of the invention that is required to achieve a transparent composition ranges from 1:5 to 5:1, for example from 1:4 to 4:1, for example from 1:3 to 3:1, for example from 1:2 to 2:1, for example from 1:2 to 1:1.

According to anyone of the invention embodiments, a composition of the invention is a transparent composition and the weight ratio between the vegetable oil and the solubilizer of the invention ranges from 1:5 to 5:1, for example from 1:4 to 4:1, for example from 1:3 to 3:1, for example from 1:2 to 2:1, for example from 1:2 to 1:1.

Surfactant System

The surfactant system of the composition comprises at least one sultaine surfactant and one taurate surfactant.

It may also comprise additional cationic, anionic, amphoteric and/or non-ionic surfactants.

Sultaine Surfactant

The composition of the invention comprises at least one amphoteric surfactant chosen from sultaine surfactants.

According to any one of the invention embodiments, the composition of the present invention comprises a sultaine surfactant of formula:

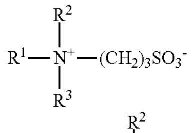

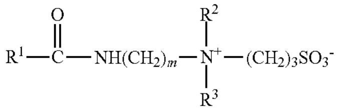

where m is 2 or 3, or variants of these (hydroxysultaines) in which $—(CH_2)_3SO_3^-$ is replaced by:

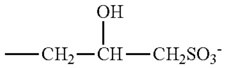

where $R^1$ is a substituted or unsubstituted alkyl or alkenyl group having 7 to 22 carbon atoms, and $R^2$ and $R^3$ are each independently alkyl, hydroxyalkyl or carboxyalkyl of 1 to 6 carbon atoms.

According to one of the invention embodiments, the sultaine surfactant is a hydroxysultaine, especially of formula:

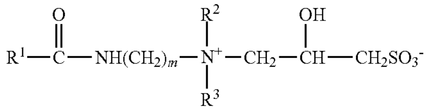

where $R^1$ is a residue of a fatty acid, and $R^2$ and $R^3$ are each independently alkyl of 1 to 6 carbon atoms, for instance methyl groups.

Fatty acids obtained from natural oils often include mixtures of fatty acids. For example the fatty acid obtained from coconut oil contains a mixture of fatty acids including C12 lauric acid, C14 myristic acid, C16 palmitic acid and C8 caprylic acid.

$R^1$ may include the residue of one or more naturally occurring fatty acids and/or of one or more synthetic fatty acids.

Examples of carboxylic acids from which $R^1$ may be derived residue of include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic acid, lignoceric acid, naturally occurring fatty acids such as those obtained from coconut oil, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof.

Most preferably $R^1$ comprises the residue of lauric acid, that is a saturated fatty acid having 12 carbon atoms, or the residue of mixed fatty acids derived from coconut oil.

According to one of the invention embodiments, the sultaine surfactant is a cocamidopropyl hydroxysultaine.

As demonstrated in Example 1, it has been found unexpectedly that the specific use of a sultaine surfactant in a composition of the present invention makes it possible to obtain a very good compromise between the following attributes: viscosity of the composition, transparency of the composition and conditioning on target area, compared to a composition having no sultaine at all, or compared to a composition including another amphoteric surfactant, such as cocamidopropyl betaine. When a sultaine surfactant of the invention is used, the above attributes are all improved in comparison with a formulation containing a cocamidopropyl betaine surfactant as amphoteric surfactant.

Similar results have been obtained when the amphoteric surfactant of the invention is replaced in Formulation 1 of the invention by a cocobetain or by a cocoamphoacetate.

In both cases, there is a decrease in the viscosity of the formulation and at the same time the formulation becomes turbid.

In contrast a formulation of the invention including a sultaine surfactant of the invention as amphoteric surfactant is transparent and exhibit a greater viscosity. According to anyone of the invention embodiments, the sultaine surfactant is present in an amount ranging from 0.1 to 10 pbw relative to the total weight of the composition, for example from 0.5 to 9 pbw, for example from 1 to 8 pbw, for example from 1.5 to 7 pbw.

According to any one of the invention embodiments, the composition of the present invention each comprise, based on 100 pbw of such composition, from 0 to less than 2 pbw of any additional amphoteric surfactant different from a sultaine surfactant of the invention.

In particular, according to any one of the invention embodiments, the composition of the present invention each comprise, based on 100 pbw of such composition, from 0 to less than 2 pbw of one amidobetaine, such as for example cocamidopropyl betaine.

More typically the composition of the present invention each comprise, based on 100 pbw of such composition, from 0 to less than 1 pbw of amidobetaine (for example cocamidopropyl betaine), and even substantially no amidobetaine, i.e. from 0 to less than 0.1 pbw amidobetaine per 100 pbw of the composition, more typically no amidobetaine, i.e. 0 pbw amidobetaine per 100 pbw of the composition.

Taurate Surfactant

The composition of the invention comprises at least one anionic surfactant chosen from taurate surfactants.

According to any one of the invention embodiments, the composition of the present invention comprises at least one methyl alkyl taurate of formula $R^aCON(CH_3)CH_2CH_2SO_3X^a$, in which $R^a$ is a linear or branched alkyl group or alkenyl group having 6 to 30, for instance 8 to 22 carbon atoms and $X^a$ is a counterion.

The counterion $X^a$ may be an alkali metal ion, alkaline earth metal ion or ammonium ion.

The counterion $X^a$ is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

Typical examples of taurates are methyl cocoyl taurates and methyl oleoyl taurates.

According to any one of the invention embodiments, the taurate surfactant is selected from the group consisting of a methyl cocoyl taurate and a methyl oleoyl taurate. According to one of the invention embodiments, the taurate surfactant is a methyl oleyl taurate.

As demonstrated in Example 3, it has been found unexpectedly that the specific use of a methyl oleoyl taurate in a composition of the present invention makes it possible to obtain an even better compromise between the following attributes: viscosity of the composition, transparency of the composition and conditioning on target area, compared to a composition having no taurate at all, or compared to a composition including an alternative taurate such as methyl cocoyl taurate. Advantageously viscosity of a composition containing a methyl oleoyl taurate is improved, without negatively impacting its transparency (% T remains greater than 85%).

According to anyone of the invention embodiments, the taurate surfactant is present in an amount ranging from 0.1 to 10 pbw relative to the total weight of the composition, for example from 0.5 to 8 pbw, for example from 1 to 6 pbw, for example from 1.5 to 5 pbw.

Additional Anionic Surfactants

The composition of the present invention may further comprise one or more additional anionic surfactants different from the taurate surfactant of the invention.

In one specific embodiment, said additional anionic surfactants may be selected from salts of alkyl sulfates, of alkylamide sulfates, of alkyl ether sulfates, of alkylamido ether sulfates, of alkylaryl ether sulfates, of monoglyceride sulfates.

Typical examples of such surfactants include sodium lauryl sulfate (SLS), sodium laureth sulfate (SLES), ammonium lauryl sulfate (ALS) or ammonium laureth sulfate (ALES).

According to anyone of the invention embodiments, additional anionic surfactants may be present in an amount ranging from 0.1 to 25 pbw relative to the total weight of the composition, for example from 1 to 20 pbw, for example from 3 to 15 pbw, for example from 5 to 15 pbw.

In another embodiment, the composition of the invention may be a sulfate-free composition. It means that the composition of the invention may be devoided of, i.e. may not contain any anionic surfactant which is a derivative of a sulfate (0 pbw).

The term "anionic surfactant which is a derivative of a sulfate" means surfactants comprising at least one anionic group or group that can be ionized into an anionic group, chosen from sulfate functions (—OSO3H or —OSO3-).

According to this specific embodiment, the following anionic surfactants are preferably not present in the composition according to the invention: salts of alkyl sulfates, of alkylamide sulfates, of alkyl ether sulfates, of alkylamido ether sulfates, of alkylaryl ether sulfates, of monoglyceride sulfates.

For instance, according to this specific embodiment, the following anionic surfactants are preferably not present in the composition according to the invention: sodium lauryl sulfate (SLS), sodium laureth sulfate (SLES), ammonium lauryl sulfate (ALS) or ammonium laureth sulfate (ALES).

Non-Ionic Surfactants

In one specific embodiment, the composition of the present invention may further comprise one or more nonionic surfactants.

The optional additional nonionic surfactant may be selected for example from alkanolamide surfactants and glycoside surfactants.

Suitable alkanolamide surfactants are known compounds and include, for example, acetamide MEA, cocamide DEA, cocamide MEA, cocamide methyl MEA, cocamide MIPA, hydroxystearamide MEA, PEG-5 cocamide MEA, lactamide MEA, lauramide MEA and lauramide DEA, preferably cocamide MIPA or cocamide methyl MEA.

Suitable glycoside surfactants are known compounds and include, for example, (C4-C22)alkylhexosides, such as butylglucoside, nonylglucoside, decylglucoside, dodecylglucoside, hexadecylglucoside, octadecylglucoside, cocoglucoside, laurylglucoside, caproyl ethyl glucoside, caprylyl/capryl glucoside, caprylyl glucoside, (C4-C22) alkylpolyhexosides, such as butylpolyglucosides, nonylpolyglucosides, decylpolyglucosides, tetradecylpolyglucosides, hexadecylpolyglucosides, erucylpolyglucosides, (C4-C22)alkylpentosides, such as nonylarabinosides, decylarabinoside, hexadecylarabinoside, octylxyloside, nonylxyloside, decylxyloside, hexadecylxyloside, erucylxyloside, and (C4-C22)alkylpolypentosides, such as butylpolyarabinosides, nonylpolyarabinosides, decylpolyarabinosides, hexadecylpolyarabinosides, octadecylpolyarabino sides, erucylpolyarabinosides, butylpolyxylosides, nonylpolyxylosides, decylpolyxylosides, octadecylpolyxylosides, and erucylpolyxylosides, butylpoly(arabino-co-xylo)sides, nonylpoly(arabino-co-xylo)sides, decylpoly(arabino-co-xylo) sides, hexadecylpoly(arabino-co-xylo)sides, octadecylpoly (arabino-co-xylo)sides, erucylpoly(arabino-co-xylo)sides, and mixtures of any of such compounds, wherein the terminology "poly(arbino-co-xylo)side" denotes a copolymeric chain of monomeric residues of arabinose and xylose. Preferably the glycoside surfactant is decylglucoside.

According to anyone of the invention embodiments, said additional non ionic surfactants, for instance alkanolamide surfactants and/or glycoside surfactants, may be present in a concentration ranging from 0.1 to 10 pbw relative to the total weight of the composition, for example from 0.2 to 8 pbw, for example from 0.5 to 5 pbw, for example from 1 to 5 pbw.

According to any one of the invention embodiments, the weight ratio of taurate surfactant to sultaine surfactant is greater than or equal to 1, preferably is greater than 1, in a composition of the invention, based on the weight percent of each surfactant in the final composition.

According to any one of the invention embodiments, the composition of the invention further comprises of at least one additional anionic surfactant as described previously, for instance sodium lauryl sulfate, sodium laureth sulfate, ammonium lauryl sulfate, and/or ammonium laureth sulfate, and at least one nonionic surfactant chosen from alkanolamide surfactants and glycoside surfactants, and does not comprise any additional amphoteric surfactants.

The surfactant system in the composition of the invention may consist of one taurate surfactant, one sultaine surfactant (especially one hydroxysultaine surfactant), one or more additional anionic surfactants (especially sodium lauryl sulfate, sodium laureth sulfate, ammonium lauryl sulfate, and/or ammonium laureth sulfate) and one nonionic surfactant chosen from alkanolamide surfactants and glycoside surfactants.

According to any one of the invention embodiments, the total amount of surfactants in a composition of the invention ranges from 5 to 25 pbw, relative to the total weight of the composition, for instance from 7 to 22 pbw, for instance from 10 to 20 pbw.

According to any one of the invention embodiments, the total amount of surfactants in a composition of the invention is lower than 15 pbw, for instance lower than 14 pbw, for instance lower than 13 pbw, relative to the total weight of the composition.

The weight ratio of anionic surfactants to amphoteric surfactants may typically range from 1:10 to 10:1.

According to any one of the invention embodiments, the composition of the invention may comprise an anionic-rich surfactant chassis, that is to say a surfactant chassis in which the ratio of anionic surfactants to amphoteric surfactants is greater than 1, for instance greater than 2.

In another embodiment of the invention, the composition of the invention may comprise an amphoteric-rich surfactant chassis, that is to say a surfactant chassis in which the ratio of amphoteric surfactants to anionic surfactants is greater than 1, for instance greater than 2.

Conditioning Agent

According to anyone of the invention embodiments, the composition of the invention may further comprises a conditioning agent, especially a cationic or ampholytic conditioning agent.

Such agents can assist in oil deposition. They might also provide some conditioning effects.

They can for example enhance the appearance and feel of hair, increase hair body or suppleness, facilitate combing and styling, improve gloss or sheen and improve the texture of hair that has been damaged by chemical or physical action. They can provide anti-static effect, in altering the static electrical properties of hair. They may also enhance softness of the skin.

They might also contribute to achieve a good compromise between the following attributes: viscosity of the composition and conditioning on target area, compared to a composition having no conditioning agent at all. They generally negatively impact transparency of the composition.

According to any one of the invention embodiments the conditioning agent may be a cationic cellulose.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

In another embodiment, the conditioning agent may be a cationic polysaccharide polymer, especially a cationic guar gum derivative, such as guar hydroxypropyltrimonium chloride (Commercially available from Rhodia in their JAGUAR trademark series).

In one specific embodiment, the conditioning agent may be a derivatized guar comprising cationic substituent groups and non ionic substituent groups.

Derivatized guars are polymers obtained by chemically modifying guar gum. The chemical modification is often referred to as derivatization. The modification provides side groups on the guar polymer backbone. The side groups are usually linked to the backbone by ether linkage. The oxygen of the ether linkage corresponds to hydroxyl groups on the guar backbone, reacted for modification. Guar comes from guar gum, the mucilage found in the seed of the leguminous plant Cyamopsis tetragonolobus. The guar seeds used to make guar gum are composed of a pair of tough, non-brittle endosperm sections, hereafter referred to as "guar splits," between which is sandwiched the brittle embryo (germ). After dehulling, the seeds are split, the germ (43-47 pbw of the seed) is removed by screening. The splits typically contain about 78-82 pbw guar gum and minor amounts of some proteinaceous material, inorganic salts, water-insoluble gum, and cell membranes, as well as some residual seed coat and seed embryo.

The water soluble fraction (85 pbw) is called "guaran" or "guar gum" which consists of linear chains of (1,4)-.β-D mannopyranosyl units—with α-D-galactopyranosyl units attached by (1,6) linkages. The ratio of D-galactose to D-mannose is about 1:2. The backbone of guar is herein understood as comprising the mannose and the galactose groups.

Modifications by a cationic substituent group are known by the one skilled in the art.

According to any one of the invention embodiments, the cationic substituent group in the derivatized guar of the invention comprises a cationic nitrogen radical, more typically a quaternary ammonium radical.

Typical quaternary ammonium radicals are trialkylammonium radicals, such as trimethylammonium radicals, triethylammonium radicals, tributylammonium radicals, aryldialkylammonium radicals, such as benzyldimethylammonium radicals, and ammonium radicals in which the nitrogen atom is a member of a ring structure, such as pyridinium radicals and imidazoline radicals, each in combination with a counterion, typically a chloride, bromide, or iodide counterion.

According to any one of the invention embodiments, the cationic substituent group is linked to the reactive functional group of the cationizing agent, for example, by an alkylene or oxyalkylene linking group. Suitable cationizing reagents include, for example, epoxy-functional cationic nitrogen compounds, such as, for example, 2,3-epoxypropyltrimethylammonium chloride; chlorohydrin-functional cationic nitrogen compounds, such as, for example, 3-chloro-2-hydroxypropyl trimethylammonium chloride, 3-chloro-2-hydroxypropyl-lauryldimethylammonium chloride, 3-chloro-2-hydroxypropyl-stearyldimethylammonium chloride; and vinyl-, or (meth)acrylamide-functional nitrogen compounds, such as methacrylamidopropyl trimethylammonium chloride.

According to any one of the invention embodiments the cationic substituent group may be for example hydroxypropyl ammonium. These can be obtained for example by reacting guar gum with compounds such as 2,3-epoxypropyltrimethylammonium chloride or 3-chloro-2-hydroxypropyltrimethylammonium chloride. Guars bearing only such cationic substituent groups are referred to, according to INCI terminology, as Guar Hydroxypropyltrimonium Chloride. Jaguar C14S provided by Rhodia is a typical example of Guar Hydroxypropyltrimonium Chloride.

Modifications by a non ionic substituent group are known by the one skilled in the art.

According to any one of the invention embodiments, the non ionic substituent group in the derivatized guar of the invention comprises a hydroxyalkyl and/or poly(alkyleneoxy) radical.

Hydroxyalkyl and/or poly(alkyleneoxy) radicals can be typically added to the guar polysaccharide chains by reacting the guar with an alkylene oxide derivatizing agent, such as ethylene oxide, propylene oxide, or butylene oxide, under known alkoxylation conditions According to any one of the invention embodiments, the non ionic substituent group in the derivatized guar of the invention comprises a hydroxypropyl radical.

A hydroxypropyl radical can be typically added to the guar polysaccharide chains by reacting the guar with reactants such as propylene oxide.

Derivatized guar comprising cationic substituent groups and non ionic substituent groups are known by the one skilled in the art. Some are referred to, according to INCI terminology, as Hydroxypropyl Guar Hydroxypropyltrimonium Chloride.

According to any one of the invention embodiments, the derivatized guar of the invention is a Hydroxypropyl Guar Hydroxypropyltrimonium Chloride.

Jaguar C162 provided by Rhodia is a typical example of Hydroxypropyl Guar Hydroxypropyltrimonium Chloride.

Jaguar LS, which is also a Hydroxypropyl Guar Hydroxypropyltrimonium Chloride provided by Rhodia, is particularly suitable as derivatized guar of the invention.

According to any one of the invention embodiments, the degree of modification by the non ionic substituent group (molar substitution or MS) is preferably between 0.1 and 1.2, preferably of between 0.3 and 0.7.

According to any one of the invention embodiments, the degree of modification by the cationic substituent group (degree of substitution or DS) is preferably between 0.01 and 0.6, preferably between 0.05 and 0.20.

According to any one of the invention embodiments, the derivatized guar of the invention has a weight-average molar mass of at least 10,000 g/mol, and more preferably of higher than 100,000 g/mol, preferably of higher than 500,000 g/mol, for example of from 500,000 g/mol to 3,000,000 g/mol, for example of from 500,000 to 1,500,000 g/mol or even more, depending on their possible degree of polymerization.

As demonstrated in Example 2, it has been found unexpectedly that the specific use of a derivatized guar in a composition of the present invention makes it possible to obtain an even better compromise between the following attributes: viscosity of the composition, transparency of the composition and conditioning on target area, compared to a composition having no conditioning agent at all, or compared to a composition including another conditioning agent. In other words, the specific use of a derivatized guar in a composition of the present invention may not only deliver the expected conditioning benefits, but also positively impact the other attributes which are viscosity of the composition and transparency of the composition. It may for instance further improve its viscosity without negatively impacting its transparency (% T remains greater than 85%).

Other cationic or ampholytic conditioning agent known in the art may be used provided that they are compatible with the inventive composition.

Mention may be made especially of synthetic cationic polymers (for example polymers comprising units having a quaternary ammonium group or a tertiary ammonium group, and optionally neutral units) and of synthetic ampholytic copolymers (for example polymers comprising units having a quaternary ammonium group or a tertiary ammonium group, units having an anionic (usually acidic) group and optionally neutral units).

Conditioning agents are known by the one skilled in the art. Examples of typical conditioning agents include (INCI names): Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34 Polyquaternium-35; Polyquaternium-36; Polyquaternium-37; Polyquaternium-39; Polyquaternium-43; Polyquaternium-44; Polyquaternium-45; Polyquaternium-46; Polyquaternium-47; Polyquaternium-48; Polyquaternium-49; Polyquaternium-50; Polyquaternium-52; Polyquaternium-53; Polyquaternium-54; Polyquaternium-55; Polyquaternium-56; Polyquaternium-57; Polyquaternium-58; Polyquaternium-59; Polyquaternium-60; Polyquaternium-63; Polyquaternium-64; Polyquaternium-65; Polyquaternium-66; Polyquaternium-67; Polyquaternium-70; Polyquaternium-73; Polyquaternium-74; Polyquaternium-75; Polyquaternium-76; Polyquaternium-85; Polyquaternium-86; Polybeta-Alanine; Polyepsilon-Lysine; Polylysine; PEG-8/SMDI Copolymer; PPG-12/SMDI Copolymer; PPG-51/SMDI Copolymer; PPG-7/Succinic Acid Copolymer; IPDI/PEG-15 Cocamine Copolymer; IPDI/PEG-15 Cocamine Copolymer Dimer Dilinoleate; IPDI/PEG-15 Soyamine Copolymer; IPDI/PEG-15 Soyamine Oxide Copolymer; IPDI/PEG-15 Soyethonium Ethosulfate Copolymer; Polyquaternium-4/Hydroxypropyl Starch Copolymer; Cassia Hydroxypropyltrimonium Chloride; Chitosan Hydroxypropyltrimonium Chloride; Dextran Hydroxypropyltrimonium Chloride; Galactoarabinan Hydroxypropyltrimonium Chloride; Ginseng Hydroxypropyltrimonium Chloride; Guar Hydroxypropyltrimonium Chloride; Hydroxypropyl Guar Hydroxypropyltrimonium Chloride; Locust Bean Hydroxypropyltrimonium Chloride; Starch Hydroxypropyltrimonium Chlorid; Hydroxypropyltrimonium Hydrolyzed Wheat Starch; Hydroxypropyltrimonium Hydrolyzed Corn Starch; Hydroxypropyl Oxidized Starch PG-Trimonium Chloride; Tamarindus Indica Hydroxypropyltrimonium Chloride; Polyacrylamidopropyltrimonium Chloride; Polymethacrylamidopropyltrimonium Chloride; Polymethacrylamidopropyltrimonium Methosulfate; Propyltrimoniumchloride Methacrylamide/Dimethylacrylamide Copolymer; Acrylamide/Ethalkonium Chloride Acrylate Copolymer; Acrylamide/Ethyltrimonium Chloride Acrylate/Ethalkonium Chloride Acrylate Copolymer; Acrylates/Carbamate Copolymer; Adipic Acid/Methyl DEA Crosspolymer; Diethylene Glycol/DMAP Acrylamide/PEG-180/HDI Copolymer; Dihydroxyethyl Tallowamine/IPDI Copolymer; Dimethylamine/Ethylenediamine/Epichlorohydrin Copolymer; HEMA Glucoside/Ethylmethacrylate Trimonium Chloride Copolymer; Hydrolyzed Wheat Protein/PEG-20 Acetate Copolymer; Hydrolyzed Wheat Protein/PVP Crosspolymer; Ethyltrimonium Chloride Methacrylate/Hydroxyethylacrylamide Copolymer.

The amount of cationic or ampholytic conditioning agent in the compositions can preferably be in the range from 0.01 to 10 pbw, particularly preferably in the range from 0.1 to 5 pbw, and especially preferably in the range from 0.2 to 2 pbw, based on the compositions.

In addition to the compounds indicated above, a composition according to the invention comprises a physiologically acceptable medium.

A physiologically acceptable medium is a medium which is particularly suitable for the application of a composition of the invention to keratin materials. The physiologically acceptable medium is generally suited to the nature of the substrate to which the composition must be applied, and also to the way in which the composition must be packaged.

According to any one of the invention embodiments, the composition of the present invention comprises water in an amount of from 5 to 90 pbw, relative to the total weight of the composition.

It may comprise for instance at least 25 pbw, for instance at least 50 pbw, for instance at least 60 pbw of water, relative to the total weight of the composition.

In one embodiment, the cosmetically acceptable aqueous medium can be composed solely of water.

According to any one of the invention embodiments, the composition of the invention further comprises at least one water-miscible organic solvent.

According to this embodiment, the cosmetically acceptable aqueous medium can be composed of a mixture of water and of a cosmetically acceptable solvent, such as a lower C1-C4 alcohols or such as alkylene glycols. The lower C1-C4 alcohols are preferably chosen from ethanol, isopropanol, tert-butanol, and n-butanol. The alkylene glycols are preferably chosen from propylene glycol and glycol ethers.

According to any one of the invention embodiments, the composition of the present invention further comprise an electrolyte.

By the term "electrolyte" we mean here ionic salt totally soluble in the composition at the concentrations used.

According to any one of the invention embodiments, the electrolyte of any composition according to the invention can be selected from the group of alkali, and ammonium salts. In particular such electrolyte can be an alkali salt.

As non limiting examples, one may cite electrolyte such as NaCl or KCl.

Electrolytes may be either present in minor amounts in the various ingredients (especially surfactants) used to prepare a composition of the invention, or alternatively be added separately ("added salts"), independently from the other ingredients.

According to any one of the invention embodiments, a composition of the invention comprises less than 3 pbw of electrolytes, especially of added salts, relative to the total weight of the composition, for instance less than 2 pbw, for instance less than 1 pbw.

When an electrolyte, such as NaCl, is added in a composition of the invention, the viscosity progressively drops. Transparency is also negatively impacted: the composition turns hazy to opaque, depending on the amount of added salts.

According to any one of the invention embodiments, the composition of the invention is substantially free of added salts, i.e. comprises from 0 to less than 0.1 pbw of added salts, relative to the total weight of the composition. A composition of the invention may even comprise no added salts, i.e. 0 pbw of added salts per 100 pbw of the composition.

The composition of the invention may further comprise additional optional ingredients which may bring specific benefits for the intended use. Such optional ingredients may include colorants, pearlescent agents, emollients, hydrating agents, opacifiers, preservatives and pH adjusters. The skilled person is able to select according to general knowledge in the art of formulating personal care compositions such as shampoos, shower gels and liquid hand soaps, and the vast literature there-related, appropriate such optional ingredients for application purposes.

In one embodiment, the composition of the present invention further comprises one or more benefit agents, such as emollients, moisturizers, conditioners, skin conditioners, or hair conditioners such as silicones such as volatile silicones, gums or oils, or non-amino silicones and mixtures thereof, mineral oils, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A, C, D, E, K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as alnus, arnica, artemisia capillaris, asiasarum root, calendula, chamomile. Cnidium, comfrey, fennel, galla rhois, hawthorn, houttuynia, hypericum, jujube, kiwi, licorice, magnolia, olive, peppermint, philodendron, salvia, sasa albomarginata, imidazoles such as ketoconazole and elubiol; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacaleitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In one embodiment, the composition of the present invention comprises a benefit agent selected from insoluble or partially insoluble ingredients such as moisturizers or conditioners, hair coloring agents, anti-UV agents, anti-wrinkle agents, fragrances or essential oils, skin-coloring agents, anti-dandruff agents, and provides enhanced deposition of such benefit agent on the substrate, ex. hair and/or skin.

In one embodiment, the personal care composition of the present invention further comprises from about 0.1 to about 50 pbw, more typically from about 0.3 to about 25 pbw, and still more typically from about 0.5 to 10 pbw, of one or more benefit agents.

The composition according to the present invention may optionally further comprise other ingredients, such as, for example, preservatives such as benzyl alcohol, methyl paraben, propyl paraben, imidazolidinyl urea, sodium benzoate, potassium sorbate, salicylic acid, methylchloroisothiazolinone and methylisothiazolinone, thickeners such as high molecular weight crosslinked polyacrylic acid (carbomer), PEG diester of stearic acid and the like, and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In general, a composition of the present invention may optionally comprise, based on 100 pbw of the personal care composition and independently for each such ingredient, up to about 15 pbw, preferably from 0.5 pbw to about 10 pbw, of such other ingredients, depending on the desired properties of the composition.

In one specific embodiment, the composition according to the present invention further comprises a fragrance material or perfume.

As used herein, the term “fragrance material or perfume” means any organic substance or composition which has a desired olfactory property and is essentially non-toxic. Such substances or compositions include all fragrance material and perfumes that are commonly used in perfumery or personal care compositions. The compounds involved may be natural, semi-synthetic or synthetic in origin.

Preferred fragrance materials and perfumes may be assigned to the classes of substance comprising the hydrocarbons, aldehydes or esters. The fragrances and perfumes also include natural extracts and/or essences, which may comprise complex mixtures of constituents, i.e. fruits such as almond, apple, cherry, grape, pear, pineapple, orange, lemon, strawberry, raspberry and the like; musk, flower scents such as lavender, jasmine, lily, magnolia, rose, iris, carnation and the like; herbal scents such as rosemary, thyme, sage and the like; woodland scents such as pine, spruce, cedar and the like.

The Applicant has discovered that a personal care composition containing a particular combination of anionic surfactants, one of which is a taurate and another one of which is one sultaine together with a specific solubilizer, remains stable over time, even when significant amounts of fragrance materials or perfume are contained therein.

In one embodiment, the composition comprises from 0.01 to 10 pbw of the fragrance material or perfume based on the total weight of the composition. In another embodiment, the composition comprises from 0.1 to 5 pbw of the fragrance material or perfume based on the total weight of the composition. In still another embodiment, the composition comprises from 0.2 to 2 pbw of the fragrance material or perfume based on the total weight of the composition.

Additional Oil(s)

According to anyone of the invention embodiments, the composition of the invention may further comprise at least one additional oil, preferably chosen from silicone and mineral oils.

In particular, a composition of the invention may comprise one or more silicone oils.

Silicone oils are known by the one skilled in the art.

These are often referred to as polyorganosiloxanes. In the present application the terms “silicone” or “polyorganosiloxane” can be used indifferently. The term “silicone” or “polyorganosiloxane” is understood to mean any organosiloxane compound comprising alkyl groups, for example methyl groups, and/or functionalized by groups other than alkyl groups.

Silicones can be linear, cyclic, or branched polymers or oligomers of monomeric silicon/oxygen (organosiloxane) monomers, optionally bearing some further functional groups. The polymeric backbone is typically made up of alternating silicon and oxygen atoms. The silicon atoms may carry a wide variety of substituents which can be the same or different. Functional end-blocking groups may carry nitrogen or hydroxyl moieties.

The polyorganosiloxane is advantageously, in particular in shampoos and conditioners, a nonvolatile and water-insoluble polyorganosiloxane.

It advantageously exhibits a viscosity of between 1000 and 2 000 000 mPa·s, and preferably between 5000 and 500 000 mPa·s.

In particular, the polyorganosiloxane can be a polydimethylorganosiloxane (“PDMS”, INCI name: dimethicone), or a polyorganosiloxane exhibiting amine groups, for example, amodimethicone (INCI name), quaternary ammonium groups, for example, silicone quaternium −1 to −10 (INCI names), terminal or non terminal hydroxyl groups, polyoxyalkylene groups, for example polyethylene oxide and/or polypropylene oxide groups (as terminal groups, as blocks within a PDMS chain or as grafts), or several of these groups.

According to any one of the invention embodiments, the amount of silicone oil present in the composition can typically be from 0.1 to 5 pbw, relative to the total weight of composition, and in particular from 0.5 to 2 pbw.

The silicone oil (polyorganosiloxane) is preferably present in the composition in an emulsion form (liquid silicone droplets dispersed in the aqueous phase).

The silicone oil can be present in the composition in the form of:

- a microemulsion with a particle size of lower than 0.15 μm;

an emulsion with a particle size of from 0.15 μm to lower than 1 μm, or of from 1 μm to lower than 1.5 μm or of from 1.5 μm to lower than 2 μm, or from 2 μm to lower than 2.5 μm, or from 2.5 μm to lower than 4 μm, or from 4 μm to lower than 10 μm, or from 10 μm to lower than 30 μm, or from 30 μm to 100 μm. Sizes herein refer to mean sizes of the droplets.

The droplets of the emulsion can be more or less large in size. Reference may thus be made to microemulsions, to miniemulsions or to macroemulsions.

In the present patent application, the term "emulsion" covers in particular all these types of emulsion. Without wishing to be committed to any one theory, it is specified that microemulsions are generally thermodynamically stable systems generally comprising large amounts of emulsifying agents. The other emulsions are generally systems in the non-thermodynamically stable state which retain for a certain time, in the metastable state, the mechanical energy provided during the emulsification. These systems generally comprise lesser amounts of emulsifying agents.

The emulsions can be obtained by mixing the carrier, preferably aqueous carrier, the polyorganosiloxane and generally an emulsifying agent, and then emulsifying. It is possible to speak of in situ emulsification.

The compositions in the emulsion form can also be obtained by mixing the carrier, preferably aqueous carrier, with a pre-prepared emulsion of droplets comprising the polyorganosiloxane in an external phase which is preferably miscible with the cosmetically acceptable carrier, preferably of the same nature as said carrier, preferably an aqueous carrier. This embodiment may be preferred as it is simple to implement. In addition, this embodiment is particularly suitable for the implementation of cosmetic compositions in which the polyorganosiloxane is in the microemulsion form. It is possible to speak of pre-emulsification.

According to a specific embodiment, the emulsion is a microemulsion, the size of the droplets of which is less than 0.15 μm. In this embodiment, the composition preferably comprises a proportion of emulsifying agent of greater than 10 parts by weight, preferably at least 15 parts by weight, with respect to the weight of polyorganosiloxane.

The size of the microemulsion droplets can be measured on an emulsion prepared prior to this introduction into the cosmetic composition by dynamic light scattering (QELS), for example as described below. The equipment used is, for example, composed of a Spectra-Physics 2020 laser, of a Brookhaven 2030 correlator and of the associated computing. As the sample is concentrated, it is diluted in deionized water and filtered through a 0.22 μm filter in order, at the end, to be at 2 pbw. The diameter obtained is an apparent diameter. The measurements are carried out at angles of 90° and 135°. For the size measurements, in addition to the conventional analysis by cumulants, the autocorrelation function is run in three ways (the exponential sampling or EXPSAM described by Pr. Pike, the "Non Negatively Constrained Least Squares" or NNLS method and the CONTIN method described by Pr. Provencher) which each give a size distribution weighted by the scattered intensity and not by the weight or the number. The refractive index and the viscosity of the water are taken into account.

According to another specific embodiment, the emulsion is an emulsion for which the mean size of the droplets is greater than or equal to 0.15 μm, for example greater than 0.5 μm, or than 1 μm, or than 2 μm, or than 10 μm, or than 20 μm, and preferably less than 100 μm. The size of the droplets can be measured, by optical microscopy and/or laser particle sizing (Horiba LA-910 laser scattering analyzer), on an emulsion prepared prior to its introduction into the cosmetic composition or directly on the cosmetic composition diluted in water. In this embodiment, the composition preferably comprises a proportion of emulsifying agent of less than 10 pbw, with respect to the weight of polyorganosiloxane.

Emulsifying agents of use in the preparation of polyorganosiloxane emulsions are in particular non-ionic surfactants, preferably polyalkoxylated surfactants, for example chosen from alkoxylated fatty alcohols, alkoxylated triglycerides, alkoxylated fatty alcohols, alkoxylated sorbitan esters, alkoxylated fatty amines, alkoxylated di(1-phenylethyl)phenols, alkoxylated tri(1-phenylethyl)phenols and alkoxylated alkylphenols, where the number of alkoxy units, more particularly oxyethylene and/or oxypropylene units, is such that the HLB value is greater than or equal to 10.

Mention may be made, among the silicone derivatives which are soluble in the water of the composition, inter alia, of dimethicone copolyols.

As relates to the silicones which are provided in the form of dispersions which are insoluble in the water of the composition, use may suitably be made of water-insoluble and non-volatile polyorganosiloxanes, among which may be mentioned polyalkylsiloxane, polyarylsiloxane or polyalkylarylsiloxane oils, gums or resins or their water-insoluble functionalized derivatives, or their mixtures, which are non-volatile.

Said organopolyosiloxanes are regarded as water-insoluble and non-volatile if their solubility in water is less than 50 g/liter and their intrinsic viscosity is at least 3000 mPa·s at 25° C.

Mention may be made, as examples of water-insoluble and non-volatile polyorganosiloxanes or silicones, of silicone gums, such as, for example, a diphenyl dimethicone gum, and preferably the polydimethylsiloxanes exhibiting a viscosity at least equal to 6×105 mPa·s at 25° C. and more preferably still those with a viscosity of greater than 2×106 mPa·s at 25° C.

According to the invention, the water-insoluble and non-volatile polyorganosiloxane or silicone occurs in a form dispersed within the composition including it.

The water-insoluble and non-volatile polyorganosiloxane or silicone exists in the form of particles or droplets, the size of which can be chosen according to the nature of the composition or the performance desired for said composition. Generally, this size can vary from 0.01 to 70 microns.

In order to facilitate the use thereof, these polyorganosiloxanes can be dispersed or dissolved beforehand in volatile or non-volatile silicone derivatives of low viscosity and then emulsified in the composition.

Mention may be made, among these silicones of low viscosity, of volatile cyclic silicones and polydimethylsiloxanes of low weight.

Use can also be made of functionalized silicone derivatives, such as aminated derivatives, directly in the form of emulsions or starting from a preformed microemulsion. They can be compounds known under the term of aminated silicones or hydroxylated silicones.

Mention is in particular made, as polyorganosiloxanes which can be used, of:

polyorganosiloxanes comprising —$Si(CH_3)_2O$— units and —$SiY(CH_3)O$— units where Y is a —$(CH_2)_3$—$NH(CH_2)_2$—$NH_2$ or —$(CH_2)_3$—$NH_2$ group;

polyorganosiloxanes comprising —$Si(CH_3)_2O$— units and HO—$Si(CH_3)_2O$— terminal units and/or —$Si(CH_3)(OH)O$— nonterminal units;

polyorganosiloxanes comprising —$Si(CH_3)_2O$— units and —$SiY(CH_3)O$— units where Y is -LX—Zx-Palc where LX is a divalent connecting group, preferably an alkylene group, ZX is a covalent bond or a divalent joining group comprising a heteroatom, Palc is a group of formula [OE]s-[OP]1X', in which OE is a group of formula —$CH_2$—$CH_2$—O—, OP is a group of formula —$CH_2$—$CHCH_3$—O— or —$CHCH_3$—$CH_2$—O—, X' is a hydrogen atom or a hydrocarbon group, s is a mean number greater than 1 and t is a mean number greater than or equal to 0;

polyorganosiloxanes, the chain of which comprises at least one block comprising units of formula —$Si(CH_3)_2O$— units and at least one —[OE]s-$[OP]_t$-block;

polyorganosiloxanes comprising —$Si(CH_3)_2O$— units and/or —$Si(CH_3)RO$— and/or —$SiR_2O$— and/or R—$Si(CH_3)_2O$— and/or $H_3C$—$SiR_2O$— and/or R—$SiR_2O$— units, where R, which can be identical or different, is an alkyl group other than a methyl group, an aryl group, an alkylaryl group or an aralkyl group.

Examples of silicone oils that can be used include the following (INCI names): Amino Bispropyl Dimethicone, Aminopropyl Dimethicone, Aminopropyl Phenyl Trimethicone, Amodimethicone, Amodimethicone Hydroxystearate, Amodimethicone/Silsesquioxane Copolymer, Behentrimonium Dimethicone PEG-8 Phthalate, Bisamino PEG/PPG-41/3 Aminoethyl PG-Propyl Dimethicone, Bis-Aminopropyl Dimethicone, Bis-Aminopropyl/Ethoxy Aminopropyl Dimethicone, Bis-Butyldimethicone Polyglyceryl-3, Bis-Butyloxyamodimethicone/PEG-60 Copolymer, Bis($C_{13-15}$ Alkoxy) Hydroxybutamidoamodimethicone, Bis($C_{13-15}$ Alkoxy) PG-Amodimethicone, Bis-Hydroxyethoxypropyl Dimethicone Beeswax Esters, Bis-Hydroxyethoxypropyl Dimethicone Isostearate, Bis-Isobutyl PEG-14/Amodimethicone Copolymer, Bis-Isobutyl PEG-15/Amodimethicone Copolymer, Bis-PEG-1 Dimethicone, Bis-PEG-4 Dimethicone, Bis-PEG-8 Dimethicone, Bis-PEG-12 Dimethicone, Bis-PEG-20 Dimethicone, Bis-PEG-12 Dimethicone Beeswax, Bis-PEG-12 Dimethicone Candelillate, Bis-PEG-10 Dimethicone/Dimer Dilinoleate Copolymer, Bis-PEG-15 Methyl Ether Dimethicone, Bisphenylhexamethicone, Bis-Phenylpropyl Dimethicone, Bis-(Polyglyceryl-3 Oxyphenylpropyl) Dimethicone, Bis (PPG-7 Undeceneth-21) Dimethicone, Borage Seed Oil PEG-7 Dimethicone Esters, $C_{30-45}$ Alkyl Cetearyl Dimethicone Crosspolymer, $C_{26-28}$ Alkyl Dimethicone, Cetearyl Dimethicone/Vinyl Dimethicone Crosspolymer, Cetrimonium Carboxydecyl PEG-8 Dimethicone, Cetyl Triethylmonium Dimethicone PEG-8 Phthalate, Cetyl Triethylmonium Dimethicone PEG-8 Succinate, Cyclohexasiloxane, Cyclomethicone, Cyclopentasiloxane, Cyclophenylmethicone, Cyclotetrasiloxane, Cyclotrisiloxane, DEA PG-Propyl PEG/PPG-18/21 Dimethicone, Dilinoleamidopropyl Dimethylamine, Dimethicone, Dimethicone PEG-7 Phosphate, Dimethicone Hydroxypropyl Trimonium Chloride, Dimethicone/Mercaptopropyl Methicone Copolymer, Dimethicone PEG-15 Acetate, Dimethicone PEG-8 Adipate, Dimethicone PEG-7 Avocadoate, Dimethicone PEG-8 Avocadoate, Dimethicone PEG-8 Beeswax, Dimethicone PEG-8 Borageate, Dimethicone PEG-7 Cocoate, Dimethicone PEG-7 Isostearate, Dimethicone PEG-7 Lactate, Dimethicone PEG-8 Lanolate, Dimethicone PEG-8 Meadowfoamate, Dimethicone PEG-7 Olivate, Dimethicone PEG-8 Olivate, Dimethicone PEG-8 Phosphate, Divinyldimethicone/Dimethicone Copolymer, Dimethicone PEG-7 Phthalate, Dimethicone PEG-8 Phthalate, Dimethicone PEG-7 Succinate, Dimethicone PEG-8 Succinate, Dimethicone PEG-7 Sulfate, Dimethicone PEG-7 Undecylenate, Dimethicone Propyl PG-Betaine, Dimethicone/Silsesquioxane Copolymer, Dimethiconol Arginine, Dimethiconol Cysteine, Dimethiconol Lactate, Dimethiconol Methionine, Dimethiconol Panthenol, Dimethiconol/Silsesquioxane Copolymer, Di-Methoxycinnamidopropyl Ethyldimonium Chloride Ether, Dimethoxysilyl Ethylenediaminopropyl Dimethicone, Dimethylaminopropylamido PCA Dimethicone, Diphenyl Amodimethicone, Diphenylisopropyl Dimethicone, Diphenylsiloxy Phenyl Trimethicone, Glycidoxy Dimethicone, Hexyl Dimethicone, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein PG-Propyl Methylsilanediol, Hydrolyzed Wheat Protein PG-Propyl Silanetriol, Hydroxypropyldimethicone, Isopolyglyceryl-3 Dimethicone, Isopolyglyceryl-3 Dimethiconol, Lauryl PEG-9 Polydimethylsiloxyethyl Dimethicone, Lauryl Polyglyceryl-3 Polydimethylsiloxyethyl Dimethicone, Linoleamidopropyl PG-Dimonium Chloride Phosphate Dimethicone, Methoxy Amodimethicone/Silsesquioxane Copolymer, Methyleugenyl PEG-8 Dimethicone, Methylsilanol Acetylmethionate, Methylsilanol Elastinate, Methyl Trimethicone, Nylon-611/Dimethicone Copolymer, PCA Dimethicone, PEG-8 Amodimethicone, PEG-3 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-8 Distearmonium Chloride PG-Dimethicone, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10 Methyl Ether Dimethicone, PEG-11 Methyl Ether Dimethicone, PEG-32 Methyl Ether Dimethicone, PEG-10 Nonafluorohexyl Dimethicone Copolymer, PEG-12 Methyl Ether Lauroxy PEG-5 Amidopropyl Dimethicone, PEG-8 PG-Coco-Glucoside Dimethicone, PEG/PPG-28/21 Acetate Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-10/2 Dimethicone, PEG/PPG-20/23 Dimethicone, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG-4 Trifluoropropyl Dimethicone Copolymer, PEG-8 Trifluoropropyl Dimethicone Copolymer, PEG-10 Trifluoropropyl Dimethicone Copolymer, PG-Amodimethicone, Phenyl Methiconol, Phenylpropyldimethylsiloxysilicate, Phenylpropyl Ethyl Methicone, Phenyl Propyl Trimethicone, Phenyl Trimethicone, Polydimethylsiloxy PPG-13 Butyl Ether Silsesquioxane, Polyglyceryl-3 Disiloxane Dimethicone, Polyglyceryl-3 Polydimethylsiloxyethyl Dimethicone, Polysilicone-1, Polysilicone-2, Polysilicone-3, Polysilicone-4, Polysilicone-5, Polysilicone-6, Polysilicone-7, Polysilicone-8, Polysilicone-10, Polysilicone-13, Polysilicone-14, Polysilicone-18, Polysilicone-18 Cetyl Phosphate, Polysilicone-18 Stearate, PPG-12 Butyl Ether Dimethicone, PPG-12 Dimethicone, PPG-27 Dimethicone, Propoxytetramethyl Piperidinyl Dimethicone, Quaternium-80, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-20, Sodium Dimethicone PEG-7 Acetyl Methyltaurate, Stearalkonium Dimethicone PEG-8 Phthalate, Steardimonium Hydroxypropyl Panthenyl PEG-7 Dimethicone Phosphate Chloride, Steardimonium Hydroxypropyl PEG-7 Dimethicone Phosphate Chloride, Trideceth-9

PG-Amodimethicone, Trifluoropropyl Cyclopentasiloxane, Trifluoropropyl Cyclotetrasiloxane, Trifluoropropyl Dimethicone, Trimethylsiloxyamodimethicone, Trimethylsiloxyphenyl Dimethicone, Gluconamidopropyl Aminopropyl Dimethicone, Cetrimonium Dimethicone PEG-7 Phthalate, Stearyl Aminopropyl Methicone, Myristylamidopropyl Dimethylamine Dimethicone PEG-7 Phosphate, Potassium Dimethicone PEG-7 Panthenyl Phosphate, Sodium PG-Propyldimethicone Thiosulfate Copolymer, Sodium PG-Propyl Thiosulfate Dimethicone, Tetrabutoxypropyl Trisiloxane.

According to specific embodiments, the composition of the present invention comprises a silicone oil selected from the group consisting of a dimethicone, an amodimethicone, a dimethiconol, a PEG-dimethicone, or a mixture or association thereof.

According to another embodiment, a composition of the invention comprises less than 3 pbw of silicone oils, relative to the total weight of composition, in particular less than 2 pbw, preferably less than 1 pbw.

According to this embodiment, a composition of the invention may comprise substantially no silicone oils, i.e. from 0 to less than 0.1 pbw of silicone oils per 100 pbw of the composition, for instance no silicone oils, i.e. 0 pbw of silicone oils per 100 pbw of the composition.

The composition of the present invention is used in a manner know in the art, for example, in the case of a cleanser or shampoo, by application of the cleanser or shampoo to the skin and/or hair and optionally rinsing the cleanser or shampoo off of the skin and/or hair with water.

According to any one of the invention embodiments, the composition of the invention may have a pH comprised between 4 and 11, for instance between 4 and 6.

According to any one of the invention embodiments, the composition of the invention may be prepared using a concentrated flowable composition.

The invention is also directed toward concentrates that are suitable to prepare a composition of the invention.

Concentrates including a mixture of surfactants and/or conditioning agents and/or solubilizer are advantageous as their use would reduce the need to transport a plurality of individual components.

Personal care compositions are usually prepared by mixing individual surfactants, solubilizers and conditioning agents. These components may be supplied as concentrated solutions which are diluted and/or and combined in appropriate ratios by the formulator. The invention covers any concentrate to be used as component ingredient to prepare a composition of the invention, and especially to concentrates containing limited levels of water (more advantageous from a cost and environmental perspective).

According to one embodiment, the present invention also covers any concentrate that can be used to prepare a composition of the invention.

For instance, the present invention is directed towards a concentrate C1 containing at least a non-ionic solubilizer of the invention as described previously and a sultaine surfactant of the invention as described previously. It may be for instance a concentrate C1' consisting of a non-ionic solubilizer of the invention as described previously and a sultaine surfactant of the invention as described previously, for instance a hydroxysultaine.

The present invention is also directed towards a concentrate C2 containing at least a non ionic surfactant of the invention as described previously, a sultaine surfactant of the invention as described previously and a taurate surfactant of the invention as described previously.

It may be for instance a concentrate C2' consisting of a non ionic surfactant of the invention as described previously, for instance an alkanolamide surfactant, a sultaine surfactant of the invention as described previously, for instance a hydroxysultaine, and a taurate surfactant of the invention as described previously, for instance a methyl cocoyl taurate or a methyl oleoyl taurate, especially a methyl oleoyl taurate.

The present invention also covers the use of anyone of concentrates C1, C1', C2 and/or C2' to prepare a composition of the invention.

The viscosity of the composition of the invention is satisfactory per se.

According to one embodiment, a composition of the invention may further comprise a thickener.

According to another embodiment, a composition of the invention may comprise less than 5 pwb of an additional thickener.

In particular, a composition of the invention may comprises less than 5 pbw of polymeric thickener(s), relative to the total weight of composition, for instance less than 3 pbw, for instance less than 2 pbw, for instance less than 1 pbw.

According to one embodiment, a composition of the invention may comprise substantially no polymeric thickener, i.e. from 0 to less than 0.1 pbw of polymeric thickener per 100 pbw of the composition, for instance no polymeric thickener, i.e. 0 pbw of polymeric thickener per 100 pbw of the composition.

To thicken and stabilize compositions containing vegetable oils, stabilizers such as crosslinked acrylic polymers of the Carbopol type are frequently used. However, these stabilizers can have the drawback of reducing the cosmetic performance. For instance, in the case of shampoos, using such synthetic polymers makes the hair more laden (charged or loaded) and coarser.

Therefore, according to anyone of the invention embodiments, a composition of the invention comprises less than 5 pbw of one crosslinked copolymer of methacrylic acid and of a C1-C4 alkyl acrylate, for instance one crosslinked methacrylic acid/ethyl acrylate copolymer, relative to the total weight of composition, for instance less than 3 pbw, for instance less than 2 pbw, for instance less than 1 pbw, or even comprise no, i.e. 0 pbw, of one crosslinked copolymer of methacrylic acid and of a C1-C4 alkyl acrylate, for instance one crosslinked methacrylic acid/ethyl acrylate copolymer.

EXAMPLES

The invention will now be described in further detail by way of the following non limiting examples, wherein the abbreviations have the usual meaning in the art. The temperatures are indicated in degrees centigrade (° C.) and the other parameters in the respective current units. Water amount indicated as "q.s." are intended to be "the amount required to complete to 100%".

Evaluation Methodologies

Sensorial Assessment, Half-Head Test on Fake Head

A fake head of 4 hour bleached Caucasian hair is used for the sensorial assessment. Length of hair: 40 cm. It was purchased from Kerling International Haarfabik GmbH, Donaustr. 7, D-71522 Backnang-Waldrems in Germany.

Sensorial analysis was performed by a trained expert panelist, following the standardized protocol described below.

Standard pre-washing procedure: The fake head was wetted for 1 min under tap water at 35° C. A standard shampoo of 10 wt. % active sodium laureth sulfate (SLE2S), 2 wt. % active cocamidopropyl betaine (CAPB), pH=5, was used. An amount of 12 ml of this standard shampoo was massaged into the hair for 90 seconds. The fake head was then rinsed for 3 min under running tap water at 35° C. The fake head is then combed with a medium tooth comb until the hair is detangled. The fake head is let to dry at room temperature.

Shampoo application and evaluation: The fake head was wetted for lmin under running tap water at 35° C. The hair was then divided to two equal parts: 6 ml of shampoo was added to each side of the head and massaged into the hair for 90 seconds. During this phase the foam properties were evaluated: flash foam, foam amount, foam texture. Each side of the head was then rinsed for 90 seconds under running tap water at 35° C. During this phase the ease of rinsing and the hair feel (softness) was evaluated. On wet state, the ease of detangling (using medium tooth comb), the hair feel and the hair care from roots to tips was evaluated. Each side of the fake head was then dried using the blow drier (maximum air flow and temperature). During this phase the drying time was measured. Each side of the hair was then combed (using medium tooth comb) and the hair feel, cleanliness, lightweightness, manageability, shine and softness was evaluated.

Viscosity Measurement

The viscosity of each shampoo formulation was measured after 24 hours in a temperature-controlled room (21±3° C.), using a Brookfield Viscometer Model DV-I at 10 rpm, spindle 4. The viscosity value was always taken after a stabilization time of 1 min.

Transmittance Measurement

The transparency of the formulation is judged via the transmittance value. A Perkin Elmer Lambda Bio 40 UV-Vis absorption spectrophotometer is employed. The sample was placed in a single use PS cuvette of 2.5 ml volume and 1 cm width. The intensity of the light passing through the sample and through the blank, distilled water, is measured at 600 nm. The % Transmittance is then calculated.

The following cleansing compositions were prepared. The raw materials used are identified by the INCI names and/or by the trade names. All the ingredients are expressed as active weight percent of the total formulation.

Example 1

| | Formulation 1 | Comparative Formulation A |
|---|---|---|
| Rhodapex ESB30 HA1 (Sodium Laureth Sulfate) | 4.64 | 4.64 |
| Rhodapon LS94 RPB (Sodium Lauryl Sulfate) | 4.36 | 4.36 |
| Mackam CBS 50G E (Cocamidopropyl Hydroxysultaine) | 2.13 | 0 |
| Mackam 50 ULB (Cocamidopropyl Betaine) | 0 | 2.13 |
| Geropon T-77 (Sodium Methyl Oleoyl Taurate) | 2.5 | 2.5 |
| Alkamuls PEG 16 CO (PEG 16 CO Oleate) | 0.9 | 0.9 |
| Mackamide CPA (Cocamide MIPA) | 1.5 | 1.5 |
| Citric Acid (50% active aqueous solution) | 0.13 | 0.13 |
| Coconut Oil (*Cocos Nucifera* Oil) | 0.63 | 0.63 |
| Jaguar LS (Hydroxypropyl Guar Hydroxypropyltrimonium Chloride) | 0.5 | 0.5 |
| Spectrastat (Caprylyl Glycol, Caprylhydroxamic acid, Glycerin) | 1 | 1 |
| Kukui Oil (*Aleurites Moluccana* Seed Oil) | 0.27 | 0.27 |
| Perfume | 0.4 | 0.4 |
| Panthenol | 0.2 | 0.2 |
| Tocopherol | 0.05 | 0.05 |
| De-ionized water | up to 100 | up to 100 |
| pH | 5 | 5 |
| Brookfield Viscosity at 10 rpm, spindle 4 (cP) | Between 3,000 and 4,000 | Between 1,500 and 2,500 |
| % Transmittance | 91 | 82.8 |

Formulation Protocol

In a beaker, mix melted coconut oil (around 30° C.) with kukui oil and Alkamuls PEG 16 CO, and finally add Tocopherol. Let cool down under gentle stirring. Add perfume and leave under stirring.

In a second beaker, heat 8.40 parts of water and the Geropon T-77 at 75° C. for 20 min under stiffing. Let cool down at room temperature under gentle stirring. Compensate water evaporation.

In another beaker, heat 1.5 parts of Cocamide MIPA with 7.51 parts of water at 65° C. under stirring, until homogeneous. Then add 1.88 parts of Rhodapon LS94 RPB. When homogeneous, stop heating and let the mixture under stirring until it cools back to 25-30° C. Compensate water evaporation.

In the main tank disperse Jaguar® LS in 56.27 parts of water. Add 0.05 parts of solution of 50 wt % active citric acid. Add Mackam CBS 50G E (or Mackam 50 ULB), mix 10 min at 100 rpm. Add 2.71 parts of Rhodapon LS 94 RPB under stirring, then Rhodapex ESB 30 until homogeneous. Mix 10 min at 100 rpm. Add the blend of Cocamide MIPA/Rhodapon LS 94 RPB, keep on mixing for 15 min at 100 rpm. Add Spectrastat. Adjust pH with the citric acid solution (target pH 4.8). Add the blend of oils/Alkamuls PEG 16 CO under stirring. Mix 20 min at 100 rpm, add Panthenol. Finally add the Geropon T-77 solution and stir 45 min at 120 rpm. Adjust the pH at 5, if needed.

Performances

Formulation 1, which includes the particular combination of surfactants of the invention (one of which being a taurate surfactant and the another one of which being a sultaine surfactant) together with a specific solubilizer of the invention, makes it possible to formulate high amounts of vegetable oils (total amount: 0.9 pbw of vegetable oils) and to achieve at the same time an acceptable compromise between the following attributes: viscosity of the composition, foaming properties and conditioning on target area, while maintaining transparency (% transmittance>85%).

Sensorial assessments confirmed that Formulation 1 exhibits very good conditioning properties, especially in terms of ease of detangling, softness and shine properties.

Comparative Formulation A, which contains a conventional betaine instead of a sultaine as required in the invention, is not transparent (% transmittance<85%). Its viscosity is also lower. Moreover during the sensorial assessment, less softness is evidenced in wet and dry state for Comparative Formulation A, compared to Formulation 1 of the invention.

Example 2

| | Formulation 1 | Formulation 2 |
|---|---|---|
| Rhodapex ESB30 HA1 (Sodium Laureth Sulfate) | 4.64 | 4.64 |
| Rhodapon LS94 RPB (Sodium Lauryl Sulfate) | 4.36 | 4.36 |
| Mackam CBS 50G E (Cocamidopropyl Hydroxysultaine) | 2.13 | 2.13 |
| Geropon T-77 (Sodium Methyl Oleoyl Taurate) | 2.5 | 2.5 |
| Alkamuls PEG 16 CO (PEG 16 CO Oleate) | 0.9 | 0.9 |
| Mackamide CPA (Cocamide MIPA) | 1.5 | 1.5 |
| Citric Acid (50% active aqueous solution) | 0.13 | 0.13 |
| Coconut Oil (*Cocos Nucifera* Oil) | 0.63 | 0.63 |
| Jaguar LS (Hydroxypropyl Guar Hydroxypropyltrimonium Chloride) | 0.5 | 0 |
| Spectrastat (Caprylyl Glycol, Caprylhydroxamic acid, Glycerin) | 1 | 1 |
| Kukui Oil (*Aleurites Moluccana* Seed Oil) | 0.27 | 0.27 |
| Perfume | 0.4 | 0.4 |
| Panthenol | 0.2 | 0.2 |
| Tocopherol | 0.05 | 0.05 |
| De-ionized water | up to 100 | up to 100 |
| pH | 5 | 5 |
| Brookfield Viscosity at 10 rpm, spindle 4 (cP) | Between 3,000 and 4,000 | Between 2,000 and 3,000 |
| % Transmittance | 91 | 96.8 |

Formulation Protocol

In a beaker, mix melted coconut oil (around 30° C.) with kukui oil and Alkamuls PEG 16 CO, and finally add Tocopherol. Let cool down under gentle stirring. Add perfume and leave under stirring.

In a second beaker, heat 8.40 parts of water and the Geropon T-77 at 75° C. for 20 min under stiffing. Let cool down at room temperature under gentle stirring. Compensate water evaporation.

In another beaker, heat 1.5 parts of Cocamide MIPA with 7.51 parts of water at 65° C. under stirring, until homogeneous. Then add 1.88 parts of Rhodapon LS94 RPB. When homogeneous, stop heating and let the mixture under stirring until it cools back to 25-30° C. Compensate water evaporation.

In the main tank disperse Jaguar® LS in 56.27 parts of water. Add 0.05 parts of solution of 50 wt % active citric acid. In the case of the formulation without guar, this step does not exist. Add Mackam CBS 50G E, mix 10 min at 100 rpm. Add 2.71 parts of Rhodapon LS 94 RPB under stirring, then Rhodapex ESB 30 HA1 until homogeneous. Mix 10 min at 100 rpm. Add the blend of Cocamide MIPA/Rhodapon LS 94 RPB, keep on mixing for 15 min at 100 rpm. Add Spectrastat. Adjust pH with the citric acid solution (target pH 4.8). Add the blend of oils/Alkamuls PEG 16 CO under stiffing. Mix 20 min at 100 rpm, add Panthenol. Finally add the Geropon T-77 solution and stir 45 min at 120 rpm. Adjust the pH at 5, if needed.

Performances

Formulation 1, which includes the particular combination of surfactants of the invention (one of which being a taurate surfactant and the another one of which being a sultaine surfactant) together with a specific solubilizer of the invention, and which further includes an additional conditioning agent (Jaguar LS) makes it possible to formulate high amounts of vegetable oils (total amount: 0.9 pbw of vegetable oils) and to achieve at the same time an acceptable compromise between the following attributes: viscosity of the composition, foaming properties and conditioning on target area, while maintaining transparency (% transmittance>85%).

Compared to Formulation 2 (which also includes the particular combination of surfactants of the invention together with a specific solubilizer of the invention, but which does not include any additional conditioning agent), Formulation 1 of the invention exhibits a higher viscosity while maintaining an acceptable transparency (% transmittance>85%).

Sensorial assessments confirmed that Formulation 1 exhibits very good conditioning properties, especially in terms of ease of detangling, softness and shine properties. Care was also more uniform from the root to the tip when using Formulation 1, compared to Formulation 2.

Example 3

| | Formulation 1 | Formulation 3 |
|---|---|---|
| Rhodapex ESB30 HA1 (Sodium Laureth Sulfate) | 4.64 | 4.64 |
| Rhodapon LS94 RPB (Sodium Lauryl Sulfate) | 4.36 | 4.36 |
| Mackam CBS 50G E (Cocamidopropyl Hydroxysultaine) | 2.13 | 2.13 |
| Geropon T-77 (Sodium Methyl Oleoyl Taurate) | 2.5 | 0 |
| Geropon TC-42 (Sodium Methyl Cocoyl Taurate) | 0 | 2.5 |
| Alkamuls PEG 16 CO (PEG 16 CO Oleate) | 0.9 | 0.9 |
| Mackamide CPA (Cocamide MIPA) | 1.5 | 1.5 |
| Citric Acid (50% active aqueous solution) | 0.13 | 0.13 |
| Coconut Oil (*Cocos Nucifera* Oil) | 0.63 | 0.63 |
| Jaguar LS (Hydroxypropyl Guar Hydroxypropyltrimonium Chloride) | 0.5 | 0.5 |
| Spectrastat (Caprylyl Glycol, Caprylhydroxamic acid, Glycerin) | 1 | 1 |
| Kukui Oil (*Aleurites Moluccana* Seed Oil) | 0.27 | 0.27 |
| Perfume | 0.4 | 0.4 |
| Panthenol | 0.2 | 0.2 |
| Tocopherol | 0.05 | 0.05 |
| De-ionized water | up to 100 | up to 100 |
| pH | 5 | 5 |
| Brookfield Viscosity at 10 rpm, spindle 4 (cP) | Between 3,000 and 4,000 | Between 1,500 and 2,000 |
| % Transmittance | 91 | 94 |

Formulation Protocol

In a beaker, mix melted coconut oil (around 30° C.) with kukui oil and Alkamuls PEG 16 CO, and finally add Tocopherol. Let cool down under gentle stirring. Add perfume and leave under stirring.

In a second beaker, heat 8.40 parts of water and the Geropon TC-77 at 75° C. for 20 min under stiffing. Let cool down at room temperature under gentle stirring. Compensate water evaporation. In the case of Geropon TC-42, this step does not exist.

In another beaker, heat 1.5 parts of Cocamide MIPA with 7.51 parts of water at 65° C. under stirring, until homogeneous. Then add 1.88 parts of Rhodapon LS94 RPB. When homogeneous, stop heating and let the mixture under stirring until it cools back to 25-30° C. Compensate water evaporation.

In the main tank disperse Jaguar® LS in 56.27 parts of water. Add 0.05 parts of solution of 50 wt % active citric acid. Add Mackam CBS 50G E, mix 10 min at 100 rpm.

Add 2.71 parts of Rhodapon LS 94 RPB under stirring, then Rhodapex ESB 30 HA1 until homogeneous. Mix 10 min at 100 rpm. Add the blend of Cocamide MIPA/Rhodapon LS 94 RPB, keep on mixing for 15 min at 100 rpm. Add Spectrastat. Adjust pH with the citric acid solution (target pH 4.8). Add the blend of oils/Alkamuls PEG 16 CO under stirring. Mix 20 min at 100 rpm, add Panthenol. Finally add the Geropon T-77 solution (or the Geropon TC-42) and stir 45 min at 120 rpm. Adjust the pH at 5.

Performances

Formulation 1, which includes the particular combination of surfactants of the invention (one of which being a taurate surfactant and the another one of which being a sultaine surfactant) together with a specific solubilizer of the invention, makes it possible to formulate high amounts of vegetable oils (total amount: 0.9 pbw of vegetable oils) and to achieve at the same time an acceptable compromise between the following attributes: viscosity of the composition, foaming properties and conditioning on target area, while maintaining transparency (% transmittance>85%).

Compared to Formulation 3 (which includes a methyl cocoyl taurate instead of a methyl oleoyl taurate), Formulation 1 of the invention exhibits a higher viscosity while maintaining an acceptable transparency (% transmittance>85%).

Sensorial assessments confirmed that both Formulations 1 and 2 exhibit very good conditioning properties, especially in terms of ease of detangling, softness and shine properties.

Example 4

| | Formulation 1 | Formulation 4 |
|---|---|---|
| Rhodapex ESB30 HA1 (Sodium Laureth Sulfate) | 4.64 | 4.64 |
| Rhodapon LS94 RPB (Sodium Lauryl Sulfate) | 4.36 | 4.36 |
| Mackam CBS 50G E (Cocamidopropyl Hydroxysultaine) | 2.13 | 2.13 |
| Geropon T-77 (Sodium Methyl Oleoyl Taurate) | 2.5 | 2.5 |
| Alkamuls PEG 16 CO (PEG 16 CO Oleate) | 0.9 | 0 |
| Marlowet CG (PEG-18 Castor Oil Dioleate) | 0 | 0.9 |
| Mackamide CPA (Cocamide MIPA) | 1.5 | 1.5 |
| Citric Acid (50% active aqueous solution) | 0.13 | 0.13 |
| Coconut Oil (*Cocos Nucifera* Oil) | 0.63 | 0.63 |
| Jaguar LS (Hydroxypropyl Guar Hydroxypropyltrimonium Chloride) | 0.5 | 0.5 |
| Spectrastat (Caprylyl Glycol, Caprylhydroxamic acid, Glycerin) | 1 | 1 |
| Kukui Oil (*Aleurites Moluccana* Seed Oil) | 0.27 | 0.27 |
| Perfume | 0.4 | 0.4 |
| Panthenol | 0.2 | 0.2 |
| Tocopherol | 0.05 | 0.05 |
| De-ionized water | up to 100 | up to 100 |
| pH | 5 | 5 |

-continued

| | Formulation 1 | Formulation 4 |
|---|---|---|
| Brookfield Viscosity at 10 rpm, spindle 4 (cP) | Between 3,000 and 5,000 | Between 3,000 and 5,000 |
| % Transmittance | 91 | 91.5 |

Formulation Protocol

In a beaker, mix melted coconut oil (around 30° C.) with kukui oil and Alkamuls PEG 16 CO (or Marlowet CG, or Alkamuls CRH/40-C respectively), and finally add Tocopherol. Let cool down under gentle stiffing. Add perfume and leave under stirring.

In a second beaker, heat 8.40 parts of water and the Geropon T-77 at 75° C. for 20 min under stiffing. Let cool down at room temperature under gentle stirring. Compensate water evaporation.

In another beaker, heat 1.5 parts of Cocamide MIPA with 7.51 parts of water at 65° C. under stirring, until homogeneous. Then add 1.88 parts of Rhodapon LS94 RPB. When homogeneous, stop heating and let the mixture under stiffing until it cools back to 25-30° C. Compensate water evaporation.

In the main tank disperse Jaguar® LS in 56.27 parts of water. Add 0.05 parts of solution of 50 wt % active citric acid. Add Mackam CBS 50G E, mix 10 min at 100 rpm.

Add 2.71 parts of Rhodapon LS 94 RPB under stirring, then Rhodapex ESB 30 HA1 until homogeneous. Mix 10 min at 100 rpm. Add the blend of Cocamide MIPA/Rhodapon LS 94 RPB, keep on mixing for 15 min at 100 rpm. Add Spectrastat. Adjust pH with the citric acid solution (target pH 4.8). Add the blend of oils/Alkamuls PEG 16 CO under stirring. Mix 20 min at 100 rpm, add Panthenol. Finally add the Geropon T-77 solution and stir 45 min at 120 rpm. Adjust the pH at 5.

Performances

Formulations 1 and 4, which includes the particular combination of surfactants of the invention (one of which being a taurate surfactant and the another one of which being a sultaine surfactant) together with a specific solubilizer of the invention (PEG-16 CO Oleate or PEG-18 Castor Oil Dioleate), make it possible to formulate high amounts of vegetable oils (total amount: 0.9 pbw of vegetable oils) and to achieve at the same time an acceptable compromise between the following attributes: viscosity of the composition, foaming properties and conditioning on target area, while maintaining transparency (% transmittance>85%).

During the sensorial assessment, the hair feel of Formulation 4 was less coated and less smooth during rinsing compared to Formulation 1, but the other attributes were equivalent. The same softness was obtained.

Example 5

Sensorial of Formulation 1 on skin was also evaluated by 7 panelists, one evaluation per panelist.

Sensorial profiles are set up following the norm NF ISO 13299. Panelists are regularly trained and checked using the norm NF ISO 8586.

During the product application, good spreadability is observed and moderate foam volume is generated. During the rinsing phase, nude sensation and and easiness of rinse are evidenced.

Regarding the skin feel after the application, good moisturization is experienced after 2 min of drying.

All these Examples demonstrate that the compositions according to the invention makes it possible to formulate relative high amounts of vegetable oils and to achieve at the same time an acceptable compromise between the following attributes: viscosity of the composition, foaming properties and conditioning on target area, while maintaining transparency.

The invention claimed is:

1. A cosmetic cleansing composition comprising at least:

a) one or more vegetable oil(s), in an amount of at least 0.3 pbw relative to the total weight of the composition, b) from about 2 pbw to about 40 pbw, relative to the total weight of the composition, of a surfactant system comprising at least one sultaine surfactant and at least one taurate surfactant, and c) at least 0.1 pbw, relative to the total weight of the composition, of a non-ionic solubilizer which is a mono- or poly-alkyl or alkenyl ester of an alkoxylated fatty acid, with said fatty acid being a saturated or unsaturated hydroxylated C8-C22 fatty acid.

2. The composition of claim 1, wherein the sultaine surfactant is of formula:

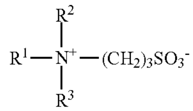

or

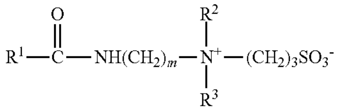

where m is 2 or 3, or variants of these in which $-(CH_2)_3SO_3^-$ is replaced by:

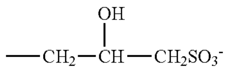

where $R^1$ is a substituted or unsubstituted alkyl or alkenyl group having 7 to 22 carbon atoms, and $R^2$ and $R^3$ are each independently alkyl, hydroxyalkyl or carboxyalkyl of 1 to 6 carbon atoms.

3. The composition of claim 2, wherein the sultaine surfactant is of formula:

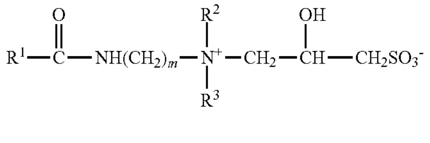

where $R^1$ is a residue of a fatty acid, and $R^2$ and $R^3$ are each independently alkyl of 1 to 6 carbon atoms.

4. The composition of claim 1, wherein the sultaine surfactant is present in an amount ranging from 0.1 to 10 pbw relative to the total weight of the composition.

5. The composition of claim 1, wherein the taurate surfactant is one methyl alkyl taurate of formula $R^aCON(CH_3)CH_2CH_2SO_3X^a$, in which $R^a$ is a linear or branched alkyl group or alkenyl group having 6 to 30 carbon atoms, and $X^a$ is a counterion.

6. The composition of claim 1, wherein the taurate surfactant is present in an amount ranging from 0.1 to 10 pbw relative to the total weight of the composition.

7. The composition of claim 1, wherein the solubilizer is a mono- or poly-alkyl or alkenyl ester of an alkoxylated fatty acid, with said fatty acid being an unsaturated hydroxylated C8-C22 fatty acid.

8. The composition of claim 1, wherein the solubilizer is a mono- or poly-alkyl or alkenyl ester of an alkoxylated fatty acid, wherein the alkyl or alkenyl ester moiety derives from fatty acids having from about 8 to about 40 carbon atoms.

9. The composition of claim 1, further comprising at least one conditioning agent.

10. The composition of claim 1, further comprising at least one additional oil.

11. The composition of claim 1, wherein the weight ratio between the vegetable oil and the solubilizer ranges from 1:5 to 5:1.

12. The composition according to claim 1, comprising less than 3 pbw of electrolytes, relative to the total weight of the composition.

13. A method, comprising simultaneously caring for and washing keratinous materials using the composition of claim 1.

14. The composition of claim 3, wherein $R^2$ and $R^3$ are each methyl groups.

15. The composition of claim 5, wherein $R^a$ is a linear or branched alkyl group or alkenyl group having 8 to 22 carbon atoms.

16. The composition of claim 1, wherein the solubilizer comprises from 5 to 50 C2-C4 alkylene oxide units.

17. The composition of claim 9, wherein the conditioning agent is a cationic or ampholytic conditioning agent.

18. The composition of claim 10, wherein the at least one additional oil is selected from the group consisting of silicone and mineral oils.

19. The method of claim 13, wherein keratinous materials are hair or skin.

20. The composition of claim 1, wherein the surfactant system consists of at least one sultaine surfactant and at least one taurate surfactant.

21. The composition of claim 1, wherein the composition is transparent.

22. The composition of claim 21, wherein the composition has a light transmittance value of greater than or equal to 85%, wherein the light transmittance value is measured at 600 nm in a 2.5 ml polystyrene cell, 10×10 mm, using a UV/VIS spectrometer Lambda Bio 40.

23. The composition of claim 1, having an absence of silicone oil, and having an absence of mineral oil.

24. The composition of claim 1, wherein weight percent of the vegetable oil in the composition is greater than weight percent of any silicone oil, any mineral oil, any cationic conditioning agent, and any ampholytic conditioning agent optionally present in the composition.

25. The composition of claim 24, wherein the vegetable oil comprises at least one member of the group consisting of sunflower oil, avocado oil, jojoba oil, maize oil, sweet almond oil, soybean oil, cucumber oil, grape seed oil, sesame oil, hazelnut oil, palm oil, castor oil, walnut oil, coconut oil, apricot oil, olive oil, kukui oil, cashew nut oil and purcellin oil;

wherein the sultaine surfactant is of formula:

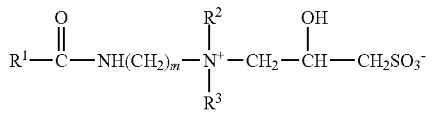

where $R^1$ is a residue of a fatty acid, and $R^2$ and $R^3$ are each independently alkyl of 1 to 6 carbon atoms, wherein the sultaine surfactant is present in an amount ranging from 0.1 to 10 pbw relative to the total weight of the composition;

wherein the taurate surfactant is a methyl cocoyl taurate or a methyl oleoyl taurate, wherein the taurate surfactant is present in an amount ranging from 0.1 to 10 pbw relative to the total weight of the composition, wherein the solubilizer is a mono- or poly-alkyl or alkenyl ester of an propoxylated fatty acid, wherein the alkyl or alkenyl ester moiety derives from fatty acids having from about 8 to about 40 carbon atoms, wherein the composition is transparent, wherein the composition has a light transmittance value of greater than or equal to 85%, wherein the light transmittance value is measured at 600 nm, comprising less than 1 pbw of electrolytes, relative to the total weight of the composition.

* * * * *